(12) United States Patent
Martino-Catt et al.

(10) Patent No.: US 6,291,224 B1
(45) Date of Patent: Sep. 18, 2001

(54) GENES CONTROLLING PHYTATE METABOLISM IN PLANTS AND USES THEREOF

(75) Inventors: Susan J. Martino-Catt, Ankeny; Hongyu Wang, Urbandale; Larry R. Beach, Des Moines, all of IA (US); Xun Wang, San Diego, CA (US); Benjamin A. Bowen, Des Moines, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/677,064

(22) Filed: Sep. 29, 2000

Related U.S. Application Data

(62) Division of application No. 09/118,442, filed on Jul. 17, 1998, now Pat. No. 6,197,561.

(51) Int. Cl.[7] ........................................... C12N 9/88

(52) U.S. Cl. ...................... 435/232; 435/69.1; 536/23.6; 800/320.1

(58) Field of Search .................................. 435/69.1, 232; 536/23.6; 800/320.1

(56) References Cited

PUBLICATIONS

Larson et al. Linkage mapping of maize and barley myo–inositol 1–phosphate synthase DNA sequences: correspondence with a low phytic acid mutation. Theor. Appl. Genet. 1999, vol. 99, pp. 27–36.*

* cited by examiner

*Primary Examiner*—Ponnathapu Achutamurthy
*Assistant Examiner*—Christian L. Fronda
(74) *Attorney, Agent, or Firm*—Pioneer Hi-Bred International, Inc.

(57) ABSTRACT

This invention relates to newly identified polynucleotides and polypeptides, variants and derivatives of same; methods for making the polynucleotides, polypeptides, variants, derivatives and antagonists. In particular the invention relates to polynucleotides and polypeptides of the phytate metabolic pathway.

2 Claims, No Drawings

SEQUENCE LISTING

<160> NUMBER OF SEQ ID NOS: 31

<210> SEQ ID NO 1
<211> LENGTH: 3252
<212> TYPE: DNA
<213> ORGANISM: Zea mays
<220> FEATURE:
<221> NAME/KEY: CDS
<222> LOCATION: (258)...(2666)
<221> NAME/KEY: misc_feature
<222> LOCATION: (1)...(3252)
<223> OTHER INFORMATION: n = A,T,C or G

<400> SEQUENCE: 1

```
gtcgacccac gcgtccgctc gccgcgggag tcacgcaacc gccgtctcct cgccggcacg      60
cttcgccgcc gccgcctctc tcctcctcgt ctcaaccgcc gcctgcacac gcagaaaagg     120
agggagaata agaggatcag caaacccaa  gccctccact cgtcgccccc tgctgcaatc     180
gccccacccg cctccgcccg ccgccgcttc tcctcacctt cctctcccgc gacatctcag     240
ttcttcatca ccaaaag atg gtc ggc ggc ggc aac gag ttc cgt ttc ttc        290
                Met Val Gly Gly Gly Asn Glu Phe Arg Phe Phe
                 1               5                    10 ttg tcc tgc gac atc agc cac ccg ctt gcc ttc cgt gtt ctc cac gca       338
Leu Ser Cys Asp Ile Ser His Pro Leu Ala Phe Arg Val Leu His Ala
             15                  20                  25 gaa cat atc ttg ttg acc gac caa aaa gtc cca gag ctc ttt gtt gag       386
Glu His Ile Leu Leu Thr Asp Gln Lys Val Pro Glu Leu Phe Val Glu
         30                  35                  40 tgc aag cta tac atc gat ggg atc caa ttt ggg ttg cct gta aaa aca       434
Cys Lys Leu Tyr Ile Asp Gly Ile Gln Phe Gly Leu Pro Val Lys Thr
     45                  50                  55 agg ttg gaa cct tct gga ccg aaa tac tgt tgg aat gag ctc ata aca       482
Arg Leu Glu Pro Ser Gly Pro Lys Tyr Cys Trp Asn Glu Leu Ile Thr
 60                  65                  70                  75 tta agt acc aaa tac agg gac cta aca tcc ctc tcg cag ctt gca ttt       530
Leu Ser Thr Lys Tyr Arg Asp Leu Thr Ser Leu Ser Gln Leu Ala Phe
                 80                  85                  90 acg gtg tgg gat gtc tca tct ggt gag aac cct gag gtt gtc ggt gga       578
Thr Val Trp Asp Val Ser Ser Gly Glu Asn Pro Glu Val Val Gly Gly
             95                 100                 105 gcc acc ata ttt ctt ttt aac agc aaa agg cag ctt aaa aca gga aga       626
Ala Thr Ile Phe Leu Phe Asn Ser Lys Arg Gln Leu Lys Thr Gly Arg
        110                 115                 120 cag aag ctg cgg ctg tgg ccc aca aag gag gca gat gga gga gtc ccc       674
Gln Lys Leu Arg Leu Trp Pro Thr Lys Glu Ala Asp Gly Gly Val Pro
    125                 130                 135 acc aca act cct ggc aag gtt cct agg aat gag agg ggt gag ata gaa       722
Thr Thr Thr Pro Gly Lys Val Pro Arg Asn Glu Arg Gly Glu Ile Glu
140                 145                 150                 155 cgt ttg gaa agg ctt gtt aac aag tat gag aga ggg cag ata caa cat       770
Arg Leu Glu Arg Leu Val Asn Lys Tyr Glu Arg Gly Gln Ile Gln His
                160                 165                 170 gtt gat tgg ctt gat cgt ctt gcc ttc agt gct atg gac aaa gct atg       818
Val Asp Trp Leu Asp Arg Leu Ala Phe Ser Ala Met Asp Lys Ala Met
            175                 180                 185 gaa aaa gag tgt gag agg aag gcc aat ttg tac cct agt ctg gtt gtt       866
Glu Lys Glu Cys Glu Arg Lys Ala Asn Leu Tyr Pro Ser Leu Val Val
        190                 195                 200 gaa ttg tgc agt ttc gaa cat aga att gtc ttc cag gaa tct gga gca       914
```

```
Glu Leu Cys Ser Phe Glu His Arg Ile Val Phe Gln Glu Ser Gly Ala
    205                 210                 215 aat ttt tat aca ccg gcc cca gta tca tta tca aat gaa ctg gtt act         962
Asn Phe Tyr Thr Pro Ala Pro Val Ser Leu Ser Asn Glu Leu Val Thr
220                 225                 230                 235 gta tgg gac cct gaa ctt gga aga acc aat cca tct gag cac aag cag        1010
Val Trp Asp Pro Glu Leu Gly Arg Thr Asn Pro Ser Glu His Lys Gln
                240                 245                 250 tta aag ctt gct aag agc ttg act cgt ggg ata gtt gat aga gat cta        1058
Leu Lys Leu Ala Lys Ser Leu Thr Arg Gly Ile Val Asp Arg Asp Leu
            255                 260                 265 aaa cca agc tca aat gag aga aag tta cta caa aca att att aag ttt        1106
Lys Pro Ser Ser Asn Glu Arg Lys Leu Leu Gln Thr Ile Ile Lys Phe
        270                 275                 280 cct cct aca cgc acc ttg gaa gtg gat gag aag caa ttg gtg tgg aag        1154
Pro Pro Thr Arg Thr Leu Glu Val Asp Glu Lys Gln Leu Val Trp Lys
    285                 290                 295 ttt cgt ttc tct ttg atg tct gag aag aaa gct cta acg aaa ttt gtc        1202
Phe Arg Phe Ser Leu Met Ser Glu Lys Lys Ala Leu Thr Lys Phe Val
300                 305                 310                 315 cgc tca gtg gat tgg agt gat aac caa gaa gct aag caa gct gtt gag        1250
Arg Ser Val Asp Trp Ser Asp Asn Gln Glu Ala Lys Gln Ala Val Glu
                320                 325                 330 ttg att gga aag tgg gaa atg att gat gtg gct gat gca cta gag ctt        1298
Leu Ile Gly Lys Trp Glu Met Ile Asp Val Ala Asp Ala Leu Glu Leu
            335                 340                 345 ctc tca cct gat ttt gaa agc gac gaa gtt cgt ggt tat gct gtc agc        1346
Leu Ser Pro Asp Phe Glu Ser Asp Glu Val Arg Gly Tyr Ala Val Ser
        350                 355                 360 gta ctt gaa agg gct gat gat gaa gaa tta cag tgc tat tta ctc cag        1394
Val Leu Glu Arg Ala Asp Asp Glu Glu Leu Gln Cys Tyr Leu Leu Gln
    365                 370                 375 tta gtg caa gct ctt cgg ttt gaa aga tct gac aag tcc cgt cta gca        1442
Leu Val Gln Ala Leu Arg Phe Glu Arg Ser Asp Lys Ser Arg Leu Ala
380                 385                 390                 395 ctc ttt ctt gta aac cgt gct ttg tcc aac atc gaa att gct agc ttc        1490
Leu Phe Leu Val Asn Arg Ala Leu Ser Asn Ile Glu Ile Ala Ser Phe
                400                 405                 410 ctc cgg tgg tat ata tta gtt gag ctt cac agt cct gca tat gca aga        1538
Leu Arg Trp Tyr Ile Leu Val Glu Leu His Ser Pro Ala Tyr Ala Arg
            415                 420                 425 cga tat tat ggc aca tat gac atg ctt gaa aac agt atg atg aaa ttg        1586
Arg Tyr Tyr Gly Thr Tyr Asp Met Leu Glu Asn Ser Met Met Lys Leu
        430                 435                 440 gtt ggt agg gag gat ggg gat gaa gat gga ttt cga ctg tgg cag agt        1634
Val Gly Arg Glu Asp Gly Asp Glu Asp Gly Phe Arg Leu Trp Gln Ser
    445                 450                 455 tta acc cgg cag aca gac ctc act gct caa ttg tgt tct att atg aag        1682
Leu Thr Arg Gln Thr Asp Leu Thr Ala Gln Leu Cys Ser Ile Met Lys
460                 465                 470                 475 gat gta aga aat gta aga ggt agc gca caa aag aaa att gaa aaa ttg        1730
Asp Val Arg Asn Val Arg Gly Ser Ala Gln Lys Lys Ile Glu Lys Leu
                480                 485                 490 agg cag cta tta tca gga gtt ttc agt gag ctt aca aac ttt gat gag        1778
Arg Gln Leu Leu Ser Gly Val Phe Ser Glu Leu Thr Asn Phe Asp Glu
            495                 500                 505 cca att cgt tca cca tta gca cca act ctt ctc cta aca gga gtt gtg        1826
Pro Ile Arg Ser Pro Leu Ala Pro Thr Leu Leu Leu Thr Gly Val Val
        510                 515                 520
```

| | | |
|---|---|---|
| cct caa gaa tcg tct ata ttt aag agt gcc ttg aac cct ttg cgc ctg<br>Pro Gln Glu Ser Ser Ile Phe Lys Ser Ala Leu Asn Pro Leu Arg Leu<br>525 530 535 | | 1874 |
| aca ttt aaa aca gca aat ggc gga aca tcc aag att att tac aaa aag<br>Thr Phe Lys Thr Ala Asn Gly Gly Thr Ser Lys Ile Ile Tyr Lys Lys<br>540 545 550 555 | | 1922 |
| ggt gat gac ctc cgg caa gat cag ttg gtt att caa acg gtt tct ttg<br>Gly Asp Asp Leu Arg Gln Asp Gln Leu Val Ile Gln Thr Val Ser Leu<br>560 565 570 | | 1970 |
| atg gac cga cta ctc aaa tta gaa aat cta gat ttg cac ctt act cca<br>Met Asp Arg Leu Leu Lys Leu Glu Asn Leu Asp Leu His Leu Thr Pro<br>575 580 585 | | 2018 |
| tac cga gtt ctt gca act gga caa gat gaa ggg atg ctt gaa ttt att<br>Tyr Arg Val Leu Ala Thr Gly Gln Asp Glu Gly Met Leu Glu Phe Ile<br>590 595 600 | | 2066 |
| agt tcc agt tct ctt gca cag att cta tca gaa cat cgc agt att aca<br>Ser Ser Ser Ser Leu Ala Gln Ile Leu Ser Glu His Arg Ser Ile Thr<br>605 610 615 | | 2114 |
| agt tac cta cag aag ttc cat cnt gat gag gat ggt cct ttt ggt ata<br>Ser Tyr Leu Gln Lys Phe His Xaa Asp Glu Asp Gly Pro Phe Gly Ile<br>620 625 630 635 | | 2162 |
| acg gct caa tgt ttg gag aca ttc ata aaa agc tgc gcc ggt tac tct<br>Thr Ala Gln Cys Leu Glu Thr Phe Ile Lys Ser Cys Ala Gly Tyr Ser<br>640 645 650 | | 2210 |
| gtc att aca tac ata ttg ggg gtt gga gac agg cat ctg gat aat ctt<br>Val Ile Thr Tyr Ile Leu Gly Val Gly Asp Arg His Leu Asp Asn Leu<br>655 660 665 | | 2258 |
| ctt cta act gat gat gga cgc ctt ttt cat gtt gac ttt gct ttt atc<br>Leu Leu Thr Asp Asp Gly Arg Leu Phe His Val Asp Phe Ala Phe Ile<br>670 675 680 | | 2306 |
| ctt ggg cga gac cca aag cca ttt ccg cca ccg atg aag ttg tgt aag<br>Leu Gly Arg Asp Pro Lys Pro Phe Pro Pro Pro Met Lys Leu Cys Lys<br>685 690 695 | | 2354 |
| gaa atg gtt gag gcc atg ggt ggt gca gaa agc caa tat tac aca agg<br>Glu Met Val Glu Ala Met Gly Gly Ala Glu Ser Gln Tyr Tyr Thr Arg<br>700 705 710 715 | | 2402 |
| ttc aag tcc tac tgc tgc gaa gca tac aac att ctg agg aag tcc agc<br>Phe Lys Ser Tyr Cys Cys Glu Ala Tyr Asn Ile Leu Arg Lys Ser Ser<br>720 725 730 | | 2450 |
| agt ctc att ttg aat cta ttc aag ctg atg gag cga tca ggc att ccg<br>Ser Leu Ile Leu Asn Leu Phe Lys Leu Met Glu Arg Ser Gly Ile Pro<br>735 740 745 | | 2498 |
| gac atc tct gcc gat gaa agc gga ggt ctc aag ctc cag gag aaa ttc<br>Asp Ile Ser Ala Asp Glu Ser Gly Gly Leu Lys Leu Gln Glu Lys Phe<br>750 755 760 | | 2546 |
| cgg ttg gat ctg gac gac gag gag gct ata cat ttc ttc cag gat ctt<br>Arg Leu Asp Leu Asp Asp Glu Glu Ala Ile His Phe Phe Gln Asp Leu<br>765 770 775 | | 2594 |
| atc aac gat agc gtg agt gct ctg ttc cct caa atg gtt gag acc atc<br>Ile Asn Asp Ser Val Ser Ala Leu Phe Pro Gln Met Val Glu Thr Ile<br>780 785 790 795 | | 2642 |
| cat aga tgg gct caa tat tgg cgg taacacaagc taatgtcgta gaagcaagtg<br>His Arg Trp Ala Gln Tyr Trp Arg<br>800 | | 2696 |
| tgaatctgta catgctgact gtcacaagcc acgtattaa gcgagaaacg acacttgatg | | 2756 |
| gatggaagct taggcgctta gcatttgggg ttcaagctgc nccgcatctg cgaattgatt | | 2816 |
| gggctgatgc agggcatggg caatcttctt cgtgccggtg acacccagga attcgggttg | | 2876 |
| tcagttgtca cttgtgatag tagaattccg tcacgcactg ctgtagacct atgggcattc | | 2936 |

-continued

```
gtcagatgta tatatgcgtt aatgtataaa atcaacttca gtagcaaatt tgtgaatacc    2996
ggaatacgtg atggtttagg gcctgtttgt ttaccccatg gattatataa tctggattat    3056
ttttggagga ttatataatc tggattatat aatctgagta gttctgtttg tttacccaga    3116
ttatttgagt tgttaatagg attcttttgt atgaggaaga caagaatgcc ctctatattt    3176
gtactaggtt gaaactcata tatgagatga acaatgtaac aaaaaaaaaa aaaaaaaaa     3236 aaaaaaaggg cggccg                                                    3252
```

<210> SEQ ID NO 2
<211> LENGTH: 803
<212> TYPE: PRT
<213> ORGANISM: Zea mays
<220> FEATURE:
<221> NAME/KEY: VARIANT
<222> LOCATION: (1)...(803)
<223> OTHER INFORMATION: Xaa = Any Amino Acid

<400> SEQUENCE: 2

```
Met Val Gly Gly Gly Asn Glu Phe Arg Phe Phe Leu Ser Cys Asp Ile
 1               5                  10                  15

Ser His Pro Leu Ala Phe Arg Val Leu His Ala Glu His Ile Leu Leu
            20                  25                  30

Thr Asp Gln Lys Val Pro Glu Leu Phe Val Glu Cys Lys Leu Tyr Ile
        35                  40                  45

Asp Gly Ile Gln Phe Gly Leu Pro Val Lys Thr Arg Leu Glu Pro Ser
    50                  55                  60

Gly Pro Lys Tyr Cys Trp Asn Glu Leu Ile Thr Leu Ser Thr Lys Tyr
65                  70                  75                  80

Arg Asp Leu Thr Ser Leu Ser Gln Leu Ala Phe Thr Val Trp Asp Val
                85                  90                  95

Ser Ser Gly Glu Asn Pro Glu Val Val Gly Gly Ala Thr Ile Phe Leu
            100                 105                 110

Phe Asn Ser Lys Arg Gln Leu Lys Thr Gly Arg Gln Lys Leu Arg Leu
        115                 120                 125

Trp Pro Thr Lys Glu Ala Asp Gly Gly Val Pro Thr Thr Thr Pro Gly
    130                 135                 140

Lys Val Pro Arg Asn Glu Arg Gly Glu Ile Glu Arg Leu Glu Arg Leu
145                 150                 155                 160

Val Asn Lys Tyr Glu Arg Gly Gln Ile Gln His Val Asp Trp Leu Asp
                165                 170                 175

Arg Leu Ala Phe Ser Ala Met Asp Lys Ala Met Glu Lys Glu Cys Glu
            180                 185                 190

Arg Lys Ala Asn Leu Tyr Pro Ser Leu Val Val Glu Leu Cys Ser Phe
        195                 200                 205

Glu His Arg Ile Val Phe Gln Glu Ser Gly Ala Asn Phe Tyr Thr Pro
    210                 215                 220

Ala Pro Val Ser Leu Ser Asn Glu Leu Val Thr Val Trp Asp Pro Glu
225                 230                 235                 240

Leu Gly Arg Thr Asn Pro Ser Glu His Lys Gln Leu Lys Leu Ala Lys
                245                 250                 255

Ser Leu Thr Arg Gly Ile Val Asp Arg Asp Leu Lys Pro Ser Ser Asn
            260                 265                 270

Glu Arg Lys Leu Leu Gln Thr Ile Ile Lys Phe Pro Pro Thr Arg Thr
        275                 280                 285
```

```
Leu Glu Val Asp Glu Lys Gln Leu Val Trp Lys Phe Arg Phe Ser Leu
            290                 295                 300

Met Ser Glu Lys Lys Ala Leu Thr Lys Phe Val Arg Ser Val Asp Trp
305                 310                 315                 320

Ser Asp Asn Gln Glu Ala Lys Gln Ala Val Glu Leu Ile Gly Lys Trp
                        325                 330                 335

Glu Met Ile Asp Val Ala Asp Ala Leu Glu Leu Leu Ser Pro Asp Phe
            340                 345                 350

Glu Ser Asp Glu Val Arg Gly Tyr Ala Val Ser Val Leu Glu Arg Ala
            355                 360                 365

Asp Asp Glu Leu Gln Cys Tyr Leu Leu Gln Leu Val Gln Ala Leu
            370                 375                 380

Arg Phe Glu Arg Ser Asp Lys Ser Arg Leu Ala Leu Phe Leu Val Asn
385                 390                 395                 400

Arg Ala Leu Ser Asn Ile Glu Ile Ala Ser Phe Leu Arg Trp Tyr Ile
                    405                 410                 415

Leu Val Glu Leu His Ser Pro Ala Tyr Ala Arg Arg Tyr Tyr Gly Thr
            420                 425                 430

Tyr Asp Met Leu Glu Asn Ser Met Met Lys Leu Val Gly Arg Glu Asp
            435                 440                 445

Gly Asp Glu Asp Gly Phe Arg Leu Trp Gln Ser Leu Thr Arg Gln Thr
450                 455                 460

Asp Leu Thr Ala Gln Leu Cys Ser Ile Met Lys Asp Val Arg Asn Val
465                 470                 475                 480

Arg Gly Ser Ala Gln Lys Lys Ile Glu Lys Leu Arg Gln Leu Leu Ser
                    485                 490                 495

Gly Val Phe Ser Glu Leu Thr Asn Phe Asp Glu Pro Ile Arg Ser Pro
                500                 505                 510

Leu Ala Pro Thr Leu Leu Thr Gly Val Pro Gln Glu Ser Ser
                515                 520                 525

Ile Phe Lys Ser Ala Leu Asn Pro Leu Arg Leu Thr Phe Lys Thr Ala
            530                 535                 540

Asn Gly Gly Thr Ser Lys Ile Ile Tyr Lys Lys Gly Asp Asp Leu Arg
545                 550                 555                 560

Gln Asp Gln Leu Val Ile Gln Thr Val Ser Leu Met Asp Arg Leu Leu
                565                 570                 575

Lys Leu Glu Asn Leu Asp Leu His Leu Thr Pro Tyr Arg Val Leu Ala
                580                 585                 590

Thr Gly Gln Asp Glu Gly Met Leu Glu Phe Ile Ser Ser Ser Leu
            595                 600                 605

Ala Gln Ile Leu Ser Glu His Arg Ser Ile Thr Ser Tyr Leu Gln Lys
610                 615                 620

Phe His Xaa Asp Glu Asp Gly Pro Phe Gly Ile Thr Ala Gln Cys Leu
625                 630                 635                 640

Glu Thr Phe Ile Lys Ser Cys Ala Gly Tyr Ser Val Ile Thr Tyr Ile
                    645                 650                 655

Leu Gly Val Gly Asp Arg His Leu Asp Asn Leu Leu Leu Thr Asp Asp
                660                 665                 670

Gly Arg Leu Phe His Val Asp Phe Ala Phe Ile Leu Gly Arg Asp Pro
            675                 680                 685

Lys Pro Phe Pro Pro Pro Met Lys Leu Cys Lys Glu Met Val Glu Ala
690                 695                 700

Met Gly Gly Ala Glu Ser Gln Tyr Tyr Thr Arg Phe Lys Ser Tyr Cys
```

```
                705                 710                 715                 720
Cys Glu Ala Tyr Asn Ile Leu Arg Lys Ser Ser Leu Ile Leu Asn
                    725                 730                 735

Leu Phe Lys Leu Met Glu Arg Ser Gly Ile Pro Asp Ile Ser Ala Asp
            740                 745                 750

Glu Ser Gly Gly Leu Lys Leu Gln Glu Lys Phe Arg Leu Asp Leu Asp
        755                 760                 765

Asp Glu Glu Ala Ile His Phe Phe Gln Asp Leu Ile Asn Asp Ser Val
    770                 775                 780

Ser Ala Leu Phe Pro Gln Met Val Glu Thr Ile His Arg Trp Ala Gln
785                 790                 795                 800

Tyr Trp Arg

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
ccgcttctcc tcaccttcct ct                                              22

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
tggcttgtga cagtcagcat gt                                              22

<210> SEQ ID NO 5
<211> LENGTH: 1428
<212> TYPE: DNA
<213> ORGANISM: Zea mays
<220> FEATURE:
<221> NAME/KEY: CDS
<222> LOCATION: (118)...(1176)

<400> SEQUENCE: 5
cccgggtcga cccacgcgtc cgggtgcccg cccgcacaca ccacctgtcc ccgctccgct      60
ccgctccgcg ttcccttctc tcggtcgccg ctactggcct tcgctcggtc cgccgcg atg   120
                                                                Met
                                                                  1 gtg tct ggc ggg tgc gtg ggg acg gag ggg gag gcg gac cgc gcg gcg      168
Val Ser Gly Gly Cys Val Gly Thr Glu Gly Glu Ala Asp Arg Ala Ala
          5                  10                  15 gcg cct ccg gag gcc gcg gag gag ccg gtg gtg ccg gcg cct ccc gcg      216
Ala Pro Pro Glu Ala Ala Glu Glu Pro Val Val Pro Ala Pro Pro Ala
     20                  25                  30 cgg gag gtc gtg gtg ggg tac gcg ctc acg acg aag aag gcc aag agc      264
Arg Glu Val Val Val Gly Tyr Ala Leu Thr Thr Lys Lys Ala Lys Ser
 35                  40                  45 ttc ctc cag ccc aag ctc cgg ggg ctc gcc agg aaa aag gga atc ttg      312
Phe Leu Gln Pro Lys Leu Arg Gly Leu Ala Arg Lys Lys Gly Ile Leu
 50                  55                  60                  65 ttt gtt gct att gat cag aaa cgt cca ttg tct gat caa ggt cca ttt      360
Phe Val Ala Ile Asp Gln Lys Arg Pro Leu Ser Asp Gln Gly Pro Phe
                 70                  75                  80
```

```
gac att gtt ctt cat aag ttg act gga aag ggg tgg cag caa ttg ctg        408
Asp Ile Val Leu His Lys Leu Thr Gly Lys Gly Trp Gln Gln Leu Leu
             85                  90                  95 gag gaa tat agg gag gct cac cca gaa gtt act gtt ctt gat cca cct        456
Glu Glu Tyr Arg Glu Ala His Pro Glu Val Thr Val Leu Asp Pro Pro
        100                 105                 110 ggc gca ata gca aac ttg cta gat cgc caa tct atg ctt caa gaa gta        504
Gly Ala Ile Ala Asn Leu Leu Asp Arg Gln Ser Met Leu Gln Glu Val
    115                 120                 125 tct gaa ttg gac tca ccg att gtc atg ttc tct tct gca ggt aaa gta        552
Ser Glu Leu Asp Ser Pro Ile Val Met Phe Ser Ser Ala Gly Lys Val
130                 135                 140                 145 cgc gtg cct aaa cag cta ttc att aat act gat ccc tca tca ata cca        600
Arg Val Pro Lys Gln Leu Phe Ile Asn Thr Asp Pro Ser Ser Ile Pro
                150                 155                 160 gct gca gtt agg agg gcg ggt ctc tct ctc cca ttg gtg gca aaa ccc        648
Ala Ala Val Arg Arg Ala Gly Leu Ser Leu Pro Leu Val Ala Lys Pro
            165                 170                 175 ttg gtg gcg aag tcc cat gag cta tcc ctg gct tat gat cca act tca        696
Leu Val Ala Lys Ser His Glu Leu Ser Leu Ala Tyr Asp Pro Thr Ser
        180                 185                 190 ctg acc aaa ctt gag ccc cct tta gtt ctt cag gaa ttt gtt aac cat        744
Leu Thr Lys Leu Glu Pro Pro Leu Val Leu Gln Glu Phe Val Asn His
    195                 200                 205 gtt ggt gtc atg ttt aag gtg tac att gtt ggg gat gca ata agg gtt        792
Val Gly Val Met Phe Lys Val Tyr Ile Val Gly Asp Ala Ile Arg Val
210                 215                 220                 225 gta cgt cgg ttt tca ctt cca aat gtt gat gaa ggt gat ctg tcg aat        840
Val Arg Arg Phe Ser Leu Pro Asn Val Asp Glu Gly Asp Leu Ser Asn
                230                 235                 240 aat gct ggg gta ttt cgg ttt cca agg gtc tct tgt gct gca gcc agc        888
Asn Ala Gly Val Phe Arg Phe Pro Arg Val Ser Cys Ala Ala Ala Ser
            245                 250                 255 gca gat gat gca gat ctt gac cct ggt gtt gct gaa ctt cct ccg aga        936
Ala Asp Asp Ala Asp Leu Asp Pro Gly Val Ala Glu Leu Pro Pro Arg
        260                 265                 270 cca ttg ctt gag atc ttg gca cga gag ctg cgg cga cga ctg ggt ctt        984
Pro Leu Leu Glu Ile Leu Ala Arg Glu Leu Arg Arg Arg Leu Gly Leu
    275                 280                 285 aga cta ttc aac att gat atg att agg gag cac gga aca aga gac cgg       1032
Arg Leu Phe Asn Ile Asp Met Ile Arg Glu His Gly Thr Arg Asp Arg
290                 295                 300                 305 ttt tat gtc ata gac atg aac tac ttt cct ggg tac ggc aaa atg ccc       1080
Phe Tyr Val Ile Asp Met Asn Tyr Phe Pro Gly Tyr Gly Lys Met Pro
                310                 315                 320 ggg tac gag cac gtg ttc acc gac ttc ctg ctg agc ctt gcc cag aaa       1128
Gly Tyr Glu His Val Phe Thr Asp Phe Leu Leu Ser Leu Ala Gln Lys
            325                 330                 335 gag tac aag agg cga cca agc tat agc tcc cta ggc tca ggc gaa ggg       1176
Glu Tyr Lys Arg Arg Pro Ser Tyr Ser Ser Leu Gly Ser Gly Glu Gly
        340                 345                 350 tgaaaagtga ggccgaggct actcggcggg ggtgccctgt atatgtctag catccgcaat    1236
gcgtgcgtgc gtgcgtacag atgtgctgcg tgacgggaga ggatgggtcg tagagttggg    1296
gcatcactgc atcacatcag tggccgcgat aaaaagaagc gaggactgtt gataggctgt    1356
aattaaattg ttactttgca ggtgctaact gttcatgctt caaaaaaaaa aaaaaaaaa     1416 aaagggcggc cg                                                        1428
```

```
<210> SEQ ID NO 6
<211> LENGTH: 353
<212> TYPE: PRT
<213> ORGANISM: Zea mays

<400> SEQUENCE: 6

Met Val Ser Gly Gly Cys Val Gly Thr Glu Gly Glu Ala Asp Arg Ala
 1               5                  10                  15

Ala Ala Pro Pro Glu Ala Ala Glu Glu Pro Val Val Pro Ala Pro Pro
            20                  25                  30

Ala Arg Glu Val Val Val Gly Tyr Ala Leu Thr Thr Lys Lys Ala Lys
        35                  40                  45

Ser Phe Leu Gln Pro Lys Leu Arg Gly Leu Ala Arg Lys Lys Gly Ile
 50                  55                  60

Leu Phe Val Ala Ile Asp Gln Lys Arg Pro Leu Ser Asp Gln Gly Pro
65                  70                  75                  80

Phe Asp Ile Val Leu His Lys Leu Thr Gly Lys Gly Trp Gln Gln Leu
                85                  90                  95

Leu Glu Glu Tyr Arg Glu Ala His Pro Glu Val Thr Val Leu Asp Pro
            100                 105                 110

Pro Gly Ala Ile Ala Asn Leu Leu Asp Arg Gln Ser Met Leu Gln Glu
        115                 120                 125

Val Ser Glu Leu Asp Ser Pro Ile Val Met Phe Ser Ala Gly Lys
130                 135                 140

Val Arg Val Pro Lys Gln Leu Phe Ile Asn Thr Asp Pro Ser Ser Ile
145                 150                 155                 160

Pro Ala Ala Val Arg Arg Ala Gly Leu Ser Leu Pro Leu Val Ala Lys
                165                 170                 175

Pro Leu Val Ala Lys Ser His Glu Leu Ser Leu Ala Tyr Asp Pro Thr
            180                 185                 190

Ser Leu Thr Lys Leu Glu Pro Pro Leu Val Leu Gln Glu Phe Val Asn
        195                 200                 205

His Val Gly Val Met Phe Lys Val Tyr Ile Val Gly Asp Ala Ile Arg
    210                 215                 220

Val Val Arg Arg Phe Ser Leu Pro Asn Val Asp Glu Gly Asp Leu Ser
225                 230                 235                 240

Asn Asn Ala Gly Val Phe Arg Phe Pro Arg Val Ser Cys Ala Ala Ala
                245                 250                 255

Ser Ala Asp Asp Ala Asp Leu Asp Pro Gly Val Ala Glu Leu Pro Pro
            260                 265                 270

Arg Pro Leu Leu Glu Ile Leu Ala Arg Glu Leu Arg Arg Leu Gly
        275                 280                 285

Leu Arg Leu Phe Asn Ile Asp Met Ile Arg Glu His Gly Thr Arg Asp
    290                 295                 300

Arg Phe Tyr Val Ile Asp Met Asn Tyr Phe Pro Gly Tyr Gly Lys Met
305                 310                 315                 320

Pro Gly Tyr Glu His Val Phe Thr Asp Phe Leu Leu Ser Leu Ala Gln
                325                 330                 335

Lys Glu Tyr Lys Arg Arg Pro Ser Tyr Ser Ser Leu Gly Ser Gly Glu
            340                 345                 350

Gly

<210> SEQ ID NO 7
<211> LENGTH: 1059
```

```
<212> TYPE: DNA
<213> ORGANISM: Zea mays
<220> FEATURE:
<221> NAME/KEY: misc_feature
<222> LOCATION: (1)...(1059)
<223> OTHER INFORMATION: n = A,T,C or G

<400> SEQUENCE: 7
atggtntcng gnggntgygt nggnacngar ggngargcng aycgngcngc ngcnccnccn      60
gargcngcng argarccngt ngtnccngcn ccnccngcnc gngargtngt ngtnggntay     120
gcnctnacna cnaaraargc naartcntty ctngarccna arctncgngg nctngcncgn     180
aaraarggna thctnttygt ngcnathgay caraarcgnc cnctntcnga ycarggnccn     240
ttygayathg tnctncayaa rctnacnggn aarggntggc arcarctnct ngargartay     300
cgngargcnc ayccngargt nacngtnctn gayccnccng gngcnathgc naayctnctn     360
gaycgncart cnatgctnca rggngtntcn garctngayt cnccnathgt natgttytcn     420
tcngcnggna argtncgngt nccnaarcar ctnttyatha ayacngaycc ntcntcnath     480
ccngcngcng tncgncgngc nggnctntcn ctnccnctng tngcnaarcc nctngtngcn     540
aartcncayg arctntcnct ngcntaygay ccnacntcnc tnacnaarct ngarccncn     600 ctngtnctnc argarttygt naaycaygtn gngtnatgt tyaargtnta yathgtnggn      660
gaygcnathc gngtngtncg ncgnttytcn ctnccnaayg tngaygargg ngayctntcn     720
aayaaygcng gngtntttycg nttyccncgn gtntcntgyg cngcngcntc ngcngaygay    780
gcngayctng ayccnggngt ngcngarctn cnccncngnc cnctnctnga rathctngcn     840
cgngarctnc gncgncgnct nggnctncgn ctnttyaaya thgayatgat hcgngarcay     900
ggnacncgng aycgnttyta ygtnathgay atgaaytayt tyccnggnta yggnaaratg     960
ccnggntayg arcaygtntt yacngaytty ctnctntcnc tngcncaraa rgartayaar    1020
cgncgnccnt cntaytcntc nctngcntcn ggngarggn                           1059

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
ttctctcggt cgccgctact gg                                              22

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
agcatgaaca gttagcacct                                                 20

<210> SEQ ID NO 10
<211> LENGTH: 1931
<212> TYPE: DNA
<213> ORGANISM: Zea mays

<400> SEQUENCE: 10
ggcacgagca gcagcctcct tcctcctctc actctcgctc gcgctgcgct cgctacctcg      60
```

-continued

```
cttcgcattc cattcgaaaa gaggggagga aaggcaagat gttcatcgag agcttccgcg      120
tcgagagccc ccacgtgcgg tacggcccga tggagatcga gtcggagtac cggtacgaca      180
cgacggagct ggtacacgag ggcaaggacg gcgcctcacg ctgggtcgtc cgccccaagt      240
ccgtcaagta caacttccgg accagaaccg ccgtccccaa gctcggggtg atgcttgtgg      300
ggtggggagg caacaacggg tccacgctga cggctgggqt cattgccaac agggagggga      360
tctcatgggc gaccaaggac aaggtgcagc aagccaacta ctacggctcc ctcacccacg      420
cctccaccat cagagtcggc agctacaacg gggaggagat ctatgcgccg ttcaagagcc      480
tccttcccat agtgaaccca gacgacattg tgttcggagg ctgggacatt agcaacatga      540
acctggccga ctccatgacc agggccaagg tgctggatat tgacctgcag aagcagctca      600
ggccctacat ggagtccatg gtgccacttc ccggtatcta tgatccggac ttcatcgcgg      660
ctaaccaggg ctctcgcgcc aacagtgtca tcaagggcac caagaaagaa caggtgggagc     720
agatcatcaa ggatatcagg gagtttaagg agaagaacaa agtggacaag atagttgtgt      780
tgtggactgc aaacactgaa aggtatagca atgtgtgcgc tggtctcaac gacacgatgg      840
agaatctact ggcatctgtg gacaagaacg aagcggaggt atcaccatca acactatatg      900
ccattgcctg tgtcatggaa ggggtgccgt tcatcaatgg gagcccccag aacacctttg      960
tgcctgggct gattgatctt gctataaaaa acaactgctt gattggtggt gacgacttca     1020
agagtggaca gaccaagatg aaatctgtct tggtcgattt ccttgttggt gctggaataa     1080
agcccaccte aatcgtgage tacaaccact ggggaaacaa cgatggcatg aacctgtctg     1140
cccctcaaac attcaggtcc aaggagatct ccaagagcaa cgtggtggat gacatggtct     1200
cgagcaatgc catcctctat gagcccggcg agcatcccga tcatgtcgtt gtcatcaagt     1260
atgtgccgta cgtgggagac agcaagaggg ctatggacga gtacacctca gagatcttca     1320
tgggcggcaa gaacaccatc gtgctgcaca acacctgtga ggactcgctc ctcgccgcac     1380
ctatcatcct tgatctggtg ctcttggctg agctcagcac caggatccag ctgaaagctg     1440
agggagagga caaattccac tccttccacc cggtggccac catcttgagt tacttccacca    1500
aggcacccct ggttccccct ggcacaccgg tggtgaacgc tctggccaag cagagggcga     1560
tgctggagaa catcatgagg gcctgcgttg ggctggcccc agagaacaac atgatcttgg     1620
agtacaagtg agccaagtgg cgtgccctgc agcgcgaggt tagctgctgg aagggaacta     1680
gaaaggcgag attagctgtg ggattgtgtt gggcttgtcg tgttttcttt tgcgttcttt     1740
cctagtcatt gctgttgcgc ttttgtattt gtcggacccg taactaccag ggctctgcta     1800
ttagcggcac ggagcctgta attgtattgt atgataatgt gatcgagggt gctacttccc     1860
ctcggcattc ctagtgttgg ttaaaagtcg ttcgacagca acttatcgac ccaaaaaaaa     1920
aaaaaaaaaa a                                                           1931
```

<210> SEQ ID NO 11
<211> LENGTH: 510
<212> TYPE: PRT
<213> ORGANISM: Zea mays

<400> SEQUENCE: 11

```
Met Phe Ile Glu Ser Phe Arg Val Glu Ser Pro His Val Arg Tyr Gly
  1               5                  10                  15

Pro Met Glu Ile Glu Ser Glu Tyr Arg Tyr Asp Thr Thr Glu Leu Val
             20                  25                  30

His Glu Gly Lys Asp Gly Ala Ser Arg Trp Val Val Arg Pro Lys Ser
```

-continued

```
                 35                  40                  45
Val Lys Tyr Asn Phe Arg Thr Arg Thr Ala Val Pro Lys Leu Gly Val
 50                  55                  60

Met Leu Val Gly Trp Gly Asn Asn Gly Ser Thr Leu Thr Ala Gly
65                  70                  75                  80

Val Ile Ala Asn Arg Glu Gly Ile Ser Trp Ala Thr Lys Asp Lys Val
                 85                  90                  95

Gln Gln Ala Asn Tyr Tyr Gly Ser Leu Thr His Ala Ser Thr Ile Arg
                100                 105                 110

Val Gly Ser Tyr Asn Gly Glu Ile Tyr Ala Pro Phe Lys Ser Leu
                115                 120                 125

Leu Pro Ile Val Asn Pro Asp Asp Ile Val Phe Gly Gly Trp Asp Ile
130                 135                 140

Ser Asn Met Asn Leu Ala Asp Ser Met Thr Arg Ala Lys Val Leu Asp
145                 150                 155                 160

Ile Asp Leu Gln Lys Gln Leu Arg Pro Tyr Met Glu Ser Met Val Pro
                165                 170                 175

Leu Pro Gly Ile Tyr Asp Pro Asp Phe Ile Ala Ala Asn Gln Gly Ser
                180                 185                 190

Arg Ala Asn Ser Val Ile Lys Gly Thr Lys Lys Glu Gln Val Glu Gln
                195                 200                 205

Ile Ile Lys Asp Ile Arg Glu Phe Lys Glu Lys Asn Lys Val Asp Lys
210                 215                 220

Ile Val Val Leu Trp Thr Ala Asn Thr Glu Arg Tyr Ser Asn Val Cys
225                 230                 235                 240

Ala Gly Leu Asn Asp Thr Met Glu Asn Leu Leu Ala Ser Val Asp Lys
                245                 250                 255

Asn Glu Ala Glu Val Ser Pro Ser Thr Leu Tyr Ala Ile Ala Cys Val
                260                 265                 270

Met Glu Gly Val Pro Phe Ile Asn Gly Ser Pro Gln Asn Thr Phe Val
                275                 280                 285

Pro Gly Leu Ile Asp Leu Ala Ile Lys Asn Asn Cys Leu Ile Gly Gly
                290                 295                 300

Asp Asp Phe Lys Ser Gly Gln Thr Lys Met Lys Ser Val Leu Val Asp
305                 310                 315                 320

Phe Leu Val Gly Ala Gly Ile Lys Pro Thr Ser Ile Val Ser Tyr Asn
                325                 330                 335

His Leu Gly Asn Asn Asp Gly Met Asn Leu Ser Ala Pro Gln Thr Phe
                340                 345                 350

Arg Ser Lys Glu Ile Ser Lys Ser Asn Val Val Asp Met Val Ser
                355                 360                 365

Ser Asn Ala Ile Leu Tyr Glu Pro Gly Glu His Pro Asp His Val Val
370                 375                 380

Val Ile Lys Tyr Val Pro Tyr Val Gly Asp Ser Lys Arg Ala Met Asp
385                 390                 395                 400

Glu Tyr Thr Ser Glu Ile Phe Met Gly Lys Asn Thr Ile Val Leu
                405                 410                 415

His Asn Thr Cys Glu Asp Ser Leu Leu Ala Ala Pro Ile Ile Leu Asp
                420                 425                 430

Leu Val Leu Leu Ala Glu Leu Ser Thr Arg Ile Gln Leu Lys Ala Glu
                435                 440                 445

Gly Glu Asp Lys Phe His Ser Phe His Pro Val Ala Thr Ile Leu Ser
                450                 455                 460
```

Tyr Phe Thr Lys Ala Pro Leu Val Pro Pro Gly Thr Pro Val Val Asn
465                 470                 475                 480

Ala Leu Ala Lys Gln Arg Ala Met Leu Glu Asn Ile Met Arg Ala Cys
            485                 490                 495

Val Gly Leu Ala Pro Glu Asn Asn Met Ile Leu Glu Tyr Lys
            500                 505                 510

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
ctcgctacct cgcttcgcat tccatt                                          26

<210> SEQ ID NO 13
<211> LENGTH: 26
<212> TYPE: DNA
<213> ORGANISM: Artificial Sequence
<220> FEATURE:
<223> OTHER INFORMATION: primer

<400> SEQUENCE: 13
acgccacttg gctcacttgt actcca                                          26

<210> SEQ ID NO 14
<211> LENGTH: 3546
<212> TYPE: DNA
<213> ORGANISM: Zea mays

<400> SEQUENCE: 14
ctcgctacct cgcttcgcat tccattcgag gagagcggtg agaggggagg aaaggcaaga      60
tgttcatcga gagcttccgc gtcgagagcc ccacgtgcg gtacggcccg acggagatcg     120
agtcggagta ccggtacgac acgacggagc tggtacacga gggcaaggac ggcgcctcac     180
gctgggtcgt ccgccccaag tccgtcaagt acaacttccg gaccagaacc gccgtcccca     240
agctcgggta tgtacggatg cagcggccct agcctcactc tctgtgaacc ctcctcctcc     300
cgtgctcagt caaatcctcc gtcgagatca actggtcggc gttccctcct aaatcctaat     360
gaaaatctta ctgctttgcc tgaagacgaa ccgtcgtaat tgttgacagc tacgcacaca     420
cttgcccatc cggatgcgtc aaatcagctc gatttgaaat tcgattcgat ggtgcccttt     480
tccatatttc gatcatccct cgcctactgt gcaatgatta cagaaacgtc cttttcctct     540
gaactttgtc ttaggctttt tgtcctgtgc acgtgagctg gtatcaattt gttcatgtaa     600
gatcaaattc cagcagggac gatgagcagc agacagaact cattacacta gcaaattgat     660
actaggatta ctggcaagtg tgcatacggc gcaatctgcc atcctggacc cccttttgttt    720 aattcctgtt cctatgcatg ttgcctacgt gcagctcgtt gtgtgttatg gtgtcaggct     780
gtcagccgct tgtctctgtc cgacggatga tgccaacttt tctgttctgg tggtgcaggg     840
tgatgcttgt ggggtgggga ggcaacaacg ggtccacgct gacggctggg gtcattgcca     900
acagggagtg agtagtactt aatttgtcct atattgcttt ccgttgtttt cagttattaa     960
tggcctaaca gagaactgaa ttttgttgtt ggttgtttca gggatctca tggccgacca    1020 aggacaaggt gcagcaagcc aactactacg gctcctcacc caggcctcca ccatcagagt    1080
cggcagctac aacggggagg agatctatgc gccgttcaag agcctccttc ccatggtaat    1140

-continued

| | |
|---|---|
| ctattataga cttgactaat actcttcttt ttactgaaac caaacataca taacaaagca | 1200 |
| tattccgtaa ggtgctagtt gatgttataa aatgaacctg tctttcaggc cagtggtctc | 1260 |
| aagtaaacgg aatgttaatc attgggttga aaaacaaag gttctaattt tgtgaaagga | 1320 |
| aagttaaact tagcataatg aaaagggaa gcactgtaag aaaggtgctg aaacaatcga | 1380 |
| ctcggtctgc catgttgtga tcctacttgc aagtcaaaag gttctgtggt tagcccaaag | 1440 |
| gttccagcat ctttggatta cactcgtgca gtattgacga tggtgctaac tggttgcaga | 1500 |
| ttcgcagact cggtgtttgt tatcttcttt tcatgaccaa gtgttaaact ggttttcagg | 1560 |
| tgaacccaga cgacattgtg ttcggaggct gggacattag caacatgaac ctggccgact | 1620 |
| ccatgaccag ggccaaggtg ctggatattg acctgcagaa gcagctcagg ccctacatgg | 1680 |
| agtccatggt gccacttccc cggtatctat gatccggact tcatcgcggc taaccagggc | 1740 |
| tctcgcgcca acagtgtcat caagggcacc aagaaagaac aggtggagca gatcatcaag | 1800 |
| gatatcaggt atatggatat ggatgctaac gtgccttggt gctaaggtgc acccagtgca | 1860 |
| acctaaaaca aataaatact actatgaatt tggtaaatat acatacatat cagagcatat | 1920 |
| tgtttaaccg gtgcacttag gagtctgcat ggtatgttgg acaatttgac attcgatata | 1980 |
| cagtgaccgc tcacttgcat gaggactcca caaagaacta aaactactga aagcttaagc | 2040 |
| aactattcgt agctaatgat gtatttggtg gacatggttt gaagatctag attaacgtgg | 2100 |
| ttgaagaaat atggttcact agtataagta atccattaca gaagcaatgg cttatgtagc | 2160 |
| taatgaaaca gggagtttag ggagaagaac aaagtggaca agatagttgt gttgtggact | 2220 |
| gcaaacactg aaaggtatag caatgtgtgc gctggtctca acgacacgat ggagaatcta | 2280 |
| ctggcatctg tggacaagaa cgaggcggag gtatcaccat caacactata tgccattgcc | 2340 |
| tgtgtcatgg aggggtgcc gttcatcaat gggagccccc agaacacctt tgtgcctggt | 2400 |
| gcgtggtttg gtgtgtttgc aaaagcctca tggtgttgca tttctgttcc aaagtttcat | 2460 |
| ggtgttgtat ttctgttcca aggcttatta tacctgttgc atgttcgtag ggctgattga | 2520 |
| tcttgctata aaaaacaact gcttgattgg tggtgacgac ttcaagagtg gacagaccaa | 2580 |
| gatgaaatct gtcttggtcg atttccttgt tggtgctgga ataaaggtgg gaacctagta | 2640 |
| tctctcttct attaagatga agtgttttt tggcaaatga cgttattgca ataactcttc | 2700 |
| tatattttca ttttcatgca gcccacctca atcgtgagct acaaccactt gggaaacaac | 2760 |
| gatggcatga acctgtctgc ccttcaaaca ttcaggtcca aggagatctc caagagcaac | 2820 |
| gtggtggatg acatggtctc gagcaatgcc atcctctatg agcccggcga gcatcccgat | 2880 |
| catgtcgttg tcatcaaggt ctgttagctg atctttcacc tcgttaaaag ttgacatatg | 2940 |
| caaggcagat ttacattgaa acttgtcact cttttgttgc agtatgtgcc gtacgtggga | 3000 |
| gacagcaaga gggctatgga cgagtacacc tcagagatct tcatgggcgg caagaacacc | 3060 |
| atcgtgctgc acaacacctg tgaggactcg ctcctcgccg cacctatcat ccttgatctg | 3120 |
| gtgctcttgc tgagctcag caccaggatc cagctgaaag ctgagggagg ggtaagagcc | 3180 |
| ccccaagtga ttaacctgaa agcacgctgc acgctaggtg atatagcact tttaatacct | 3240 |
| tctggtgtct ctcttatgca ggacaaattc cactccttcc acccggtggc caccatcctg | 3300 |
| agctacctca ccaaggcacc cctggtaagc cttttctcct gcatcccggc atcactgcac | 3360 |
| tgcgttttgc ttcaatccag ccactgatcg tctctcttga aacctgaaca acaggttccc | 3420 |
| cctggcacac cggtggtgaa cgctctggcc aagcagacgg cgatgctgga gaacatcatg | 3480 |

```
agggcctgcg ttgggctggc cccagagaac aacatgatcc tggagtacaa gtgagccaag    3540
tggcgt                                                               3546

<210> SEQ ID NO 15
<211> LENGTH: 3546
<212> TYPE: DNA
<213> ORGANISM: Zea mays

<400> SEQUENCE: 15
ctcgctacct cgcttcgcat tccattcgag gagagcggtg agaggggagg aaaggcaaga      60
tgttcatcga gagcttccgc gtcgagagcc cccacgtgcg gtacggcccg acggagatcg     120
agtcggagta ccggtacgac acgacggagc tggtacacga gggcaaggac ggcgcctcac     180
gctgggtcgt ccgccccaag tccgtcaagt acaacttccg gaccagaacc gccgtcccca     240
agctcgggta tgtacggatg cagcggccct agcctcactc tctgtgaacc ctcctcctcc     300
cgtgctcagt caaatcctcc gtcgagatca actggtcggc gttccctcct aaatcctaat     360
gaaaatctta ctgctttgcc tgaagacgaa ccgtcgtaat tgttgacagc tacgcacaca     420
cttgcccatc cggatgcgtc aaatcagctc gatttgaaat tcgattcgat ggtgcccttt     480
tccatatttc gatcatcctt cgcctactgt gcaatgatta cagaaacgtc cctttcctct     540
gaactttgtc ttaggctttt tgtcctgtgc acgtgagctg tatcaattt gttcatgtaa      600 gatcaaattc cagcagggac gatgagcagc agacagaact cattacgcta gcaaattgat     660
actaggatta ctgcaagtg tgcatacggc gcaatctgcc atcctggacc cccttttgttt     720 aattcctgtt cctatgcatg ttgcctacgt gcagctcgtt gtgtgttatg gtgtcaggct     780
gtcagccgct tgtctctgtc tgacggatga tgccaacttt tctgttctgg tggtgcaggg     840
tgatgcttgt gggggtgggga ggcaacaacg ggtccacgct gacggctggg gtcattgcca     900
gcagggagtg agtagtactt aatttgtcct atattgcttt ccgttgtttt cagttattaa     960
tggcctgaca gagaactgaa ttttgttgtt ggctgtttca ggggatctca tggccgacca    1020
aggacaaggt gcagcaagcc aactactacg gctcctcacc caggcctcca ccatcagagt    1080
cggcagctac aacggggagg agatctatgc gccgttcaag agcctccttc ccatggtaat    1140
ctattataga cttgactaat actcttcttt ttactgaaac caaacataca taacaaagca    1200
tattccgtaa ggtgctagtt gatgttataa agtgaacctg tctttcaggc cagtggtctc    1260
aagtaaacgg aatgttaatc attgggttga aaaacaaag gttctaattt tgtgaaagga    1320
atgttaaact tagcataatg aaaagggga gcattgtaag aaaggtgctg aaacaatcga    1380
ctcggtctgc catgttgtga tcctacttgc aagtcaaaag gttctgtggt tagctcaaag    1440
gttccagcat ctttggatta cactcgtgca gtattgacga tggtgctaac tggttgcaga    1500
ttcgcagact cggtgtttgt tatcttcctt tcatgaccaa gtgttgaact ggttttcagg    1560
tgaacccaga cgacattgtg ttcggaggct gggacattag caacatgaac ctggccgact    1620
ccatgaccag ggccaaggtg ctggatattg acctgcagaa gcagctcagg ccctacatgg    1680
agtccatggt gccacttccc cggtatctat gatccggact tcatcgcggc taaccagggc    1740
tctcgcgcca acagtgtcat caagggcacc aagaaagaac aggtggagca gatcatcaag    1800
gatatcaggt atatggatat ggatgctaac gtgccttggt gctaaggtgc acccagtgca    1860
acctaaaaca aataaatact actatgaatt tggtaaatat acatacatat cagaacatat    1920
tgtttaaccg gtgcacttag aagtctgcat ggtatgttgg acaatttgac attcgatata    1980
cagtgaccgc tcacttgcat gaggactcca caaagaacta aaactactga aagcttaagc    2040
```

```
aactattcgt agctaatgat gtatttggtg gacatggttt gaagatctag attaacgtgg   2100
ttgaagaaat atggttcact agcataagta atccattaca gaagctatgg cttatgtagc   2160
taatgaaaca gggagtttaa ggagaagaac aaagtggaca agatagttgt gttgtggact   2220
gcaaacactg aaaggtatag caatgtgtgc gctggtctca acgacacgat ggagaatcta   2280
ctggcatctg tggacaagaa cgaggcggag gtatcaccat caacactata tgccattgcc   2340
tgtgtcatgg aggggtgcc gttcatcaat gggagccccc agaacaccett tgtgcctggt    2400 gcgtggtttg gtgtgtttgc aaaagcttca tggtgttgca tttctgttcc aaagtttcat   2460
ggtgttgtat ttccgttcca aggcttatta tacctgttgc atgttcgtag gctgattga    2520 tcttgctata aaaaacaact gcttgattgg tggtgacgac ttcaagagtg gacagaccaa   2580
gatgaaatct gtcttggtcg atttccttgt tggtgctgga ataaaggtgg aacctagta    2640 tctctcttct attaagatga agtgttttt tggcaaatga cgttattgca ataactcttc    2700
tatattttca ttttcatgca gcccacctca atcgtgagct acaaccactt gggaaacaac   2760
gatggcatga acctgtctgc ccttcaaaca ttcaggtcca aggagatctc caagagcaac   2820
gtggtggatg acatggtctc gagcaatgcc atcctctatg agcccggcga gcatcccgat   2880
catgtcgttg tcatcaaggt ctgttagctg atctttcacc tcgttaaaag ttgacatatg   2940
caaggcagat ttacattgaa acttgtcact cttttgttgc agtatgtgcc gtacgtggga   3000
gacagcaaga gggctatgga cgagtacacc tcagagatct tcatgggcgg caagaacacc   3060
atcgtgctgc acaacacctg tgaggactcg ctcctcgccg cacctatcat ccttgatctg   3120
gtgctcttgg ctgagctcag caccaggatc cagctgaaag ctgagggaga ggtaagagcc   3180
ccccaagtga ttaacctgaa agcacgctgc acgctaggtg atatagcact tttaatacct   3240
tctggtgtct ctcttatgca ggacaaattc cactccttcc acccggtggc caccatcctg   3300
agctacctca ccaaggcacc cctggtaagc ctttttctcct gcatcccggc atcactgcac   3360
tgcgttttgc ttcaatccag ccactgatcg tctctctcga aacctgaaca acaggttccc   3420
cctggcacac cggtggtgaa cgctctggcc aagcagacgg cgatgctgga gaacatcatg   3480
agggcctgcg ttgggctggc cccagagaac aacatgatcc tggagtacaa gtgagccaag   3540
tggcgt                                                              3546
```

<210> SEQ ID NO 16
<211> LENGTH: 1070
<212> TYPE: DNA
<213> ORGANISM: Zea mays

<400> SEQUENCE: 16

```
cggcacgagg ttgcgggcga accgaaaatc acgggcgcga gagatcggag cacggcatgt    60
cggaggagca gttcctcgcc gtggcggtgg aagccgccaa gagcgccggc gagattattc   120
gcaagggatt ctaccagacc aagaacgtcc agcacaaggg ccaggtggat tggtgacgg    180 agacggacaa ggcctgcgag gacctcatct tcaaccacct ccggaagcac ttcccggacc   240
acaagttcat cggggaggag gagtccgcgg cgctcgggc caccgctgac ctcaccgacg   300
accccacctg gatcgtcgat cccctcgacg ggaccactaa tttcgtccat ggtttcccat   360
ttgtatgtgt ctccgttggc ctcaccattg ggaaaattcc cactgtcgga gtcgtcttca   420
accccatcat gaacgaactt ttcacggcgg ttcgtggaaa agggcttttc ctgaatggct   480
ctccaattaa agcatcatct caagatgagt tagtgaaggc tcttctggta acagaggctg   540
```

```
gaaccaatag agacaagacc actgtggatg atacaaccaa cagaatcaac aggctactat    600
acaagattcg atccatacgg atgtgtggat cattggcttt aaacatgtgt ggagttgcct    660
gtggtagact agatttgtgt tatgagatag gatttggtgg tccatgggat gttgctgctg    720
gtgctgtaat tcttcaggaa gccggtggcc ttgtttttga cccaagcggc ggagagtttg    780
atttgatgtc gcgaagaatg gcaggatcaa acagcttgct gaaggataag ttcgtcaagg    840
aactggggga tactaattga aacaaatgtt agtattattc gtggaacaga ttaagacaat    900
aaggttgccc cgccgcatgg tgattaactt attgtttggg caacaaaatt ccatgtaatt    960
ctgcacctgt acaactatgt tggacgcaga acattttatt gagttttgtg attacatggg   1020
aatacatagg ttgaggcaac ggtccctact ttaaaaaaaa aaaaaaaaaa                1070
```

<210> SEQ ID NO 17
<211> LENGTH: 267
<212> TYPE: PRT
<213> ORGANISM: Zea mays

<400> SEQUENCE: 17

```
Met Ser Glu Glu Gln Phe Leu Ala Val Ala Val Glu Ala Ala Lys Ser
 1               5                  10                  15

Ala Gly Glu Ile Ile Arg Lys Gly Phe Tyr Gln Thr Lys Asn Val Gln
            20                  25                  30

His Lys Gly Gln Val Asp Leu Val Thr Glu Thr Asp Lys Ala Cys Glu
        35                  40                  45

Asp Leu Ile Phe Asn His Leu Arg Lys His Phe Pro Asp His Lys Phe
    50                  55                  60

Ile Gly Glu Glu Ser Ala Ala Leu Gly Ala Thr Ala Asp Leu Thr
65                  70                  75                  80

Asp Asp Pro Thr Trp Ile Val Asp Pro Leu Asp Gly Thr Thr Asn Phe
                85                  90                  95

Val His Gly Phe Pro Phe Val Cys Val Ser Val Gly Leu Thr Ile Gly
            100                 105                 110

Lys Ile Pro Thr Val Gly Val Val Phe Asn Pro Ile Met Asn Glu Leu
        115                 120                 125

Phe Thr Ala Val Arg Gly Lys Gly Ala Phe Leu Asn Gly Ser Pro Ile
    130                 135                 140

Lys Ala Ser Ser Gln Asp Glu Leu Val Lys Ala Leu Leu Val Thr Glu
145                 150                 155                 160

Ala Gly Thr Asn Arg Asp Lys Thr Thr Val Asp Thr Thr Asn Arg
                165                 170                 175

Ile Asn Arg Leu Leu Tyr Lys Ile Arg Ser Ile Arg Met Cys Gly Ser
            180                 185                 190

Leu Ala Leu Asn Met Cys Gly Val Ala Cys Gly Arg Leu Asp Leu Cys
        195                 200                 205

Tyr Glu Ile Gly Phe Gly Gly Pro Trp Asp Val Ala Ala Gly Ala Val
    210                 215                 220

Ile Leu Gln Glu Ala Gly Gly Leu Val Phe Asp Pro Ser Gly Gly Glu
225                 230                 235                 240

Phe Asp Leu Met Ser Arg Arg Met Ala Gly Ser Asn Ser Leu Leu Lys
                245                 250                 255

Asp Lys Phe Val Lys Glu Leu Gly Asp Thr Asn
            260                 265
```

<210> SEQ ID NO 18

```
<211> LENGTH: 25
<212> TYPE: DNA
<213> ORGANISM: Artificial Sequence
<220> FEATURE:
<223> OTHER INFORMATION: primer

<400> SEQUENCE: 18
acgaggttgc gggcgaaccg aaaat                                    25

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
tagggaccgt tgcctcaacc tat                                      23

<210> SEQ ID NO 20
<211> LENGTH: 362
<212> TYPE: DNA
<213> ORGANISM: Zea mays
<220> FEATURE:
<221> NAME/KEY: misc_feature
<222> LOCATION: (1)...(362)
<223> OTHER INFORMATION: n = A,T,C or G

<400> SEQUENCE: 20
ggtaaagggt gcacatttna tggttgggtt gaagggccta tcaccttccc cccaacgtat    60
aaatacgagt ttaactcaga aaaatatgta antgacgcga cgaaatctgg gagaagaaca   120
cccgcatggt atgctccact agacatcaaa cttgagatat gtctatggaa ataaggaaat   180
taacatcttc acctgcttgt ataggtgtga ccgcatcctc tcgtatgggg agggacaag    240 gctactttca tacaacaggg cggagttata tnatctgatc atcgaccggt gactgcagtn   300
tatatggcag angttgaaat gtctggcccc atgaagctgc aaagagctct aanattcagc   360
aa                                                                 362

<210> SEQ ID NO 21
<211> LENGTH: 274
<212> TYPE: DNA
<213> ORGANISM: Zea mays
<220> FEATURE:
<221> NAME/KEY: misc_feature
<222> LOCATION: (1)...(274)
<223> OTHER INFORMATION: n = A,T,C or G

<400> SEQUENCE: 21
ttgngaccat gtngccgtan gcccgacgga gatcgagtcg gagtaccgta nacacgacga    60
gctngtgcac gaggccaagg acggcgcctc ccgctggtcg tccgccncaa gtccgtcaat   120
acaattccgg accagcagcg ccgtccccaa gctcgggtca tgcttgtggg gttgggaggc   180
aacaanggtc cacgctgacg gtggggtcat tggcancagg gagggatctn atggggaca    240 aggacaggtg cgcaagccaa taataaggtn ctna                              274

<210> SEQ ID NO 22
<211> LENGTH: 685
<212> TYPE: DNA
<213> ORGANISM: Zea mays
<220> FEATURE:
<221> NAME/KEY: misc_feature
<222> LOCATION: (1)...(685)
<223> OTHER INFORMATION: n = A,T,C or G
```

<400> SEQUENCE: 22

```
cntggaccac gcgtccgcga aaattgagaa acattgttca gtggacgccg ttctttcaaa      60
cttacaaaaa acagaggtat ccatgggtac agctagccgg acaccaaggc aatttcaaag     120
ccggtccgga acctggtacg atcctcaaga aactttgtcc caaagaacag ttgtgcttcc     180
aagtgctgat gaaggacgtt ctgagaccgt acgtgcccga atacaagggc cacttgacta     240
ccgacgacgg agacctatat cttcagctag aagacttgtt gggtgacttc acttcgccgt     300
gcgtcatgga ctgcaagatc ggcgtcagga cgtatctgga agangaactg gcgaaagcca     360
aagagaaacc caagttgaga aaagacatgt acgaaaaaat gattcagata daccccaacg     420
caccatcgga agangaacac cgactgaagg gtgtgacaaa accgaagtac atggtttgga     480
aggagacnat ttcgtccacn gccacgttgg gcttccggat cgaagggatc aanaaaagcn     540
atggaaaatc nagcaaggac ttccagacga caaagaaccg ggaccaggtg atcnaacctt     600
tcgagatttc ntccccngtt tcccccccgt tatccccaan tncataaacc gactganaac     660
natcaganac ttctggtgaa ctccn                                           685
```

<210> SEQ ID NO 23
<211> LENGTH: 333
<212> TYPE: DNA
<213> ORGANISM: Zea mays
<220> FEATURE:
<221> NAME/KEY: misc_feature
<222> LOCATION: (1)...(333)
<223> OTHER INFORMATION: n = A,T,C or G

<400> SEQUENCE: 23

```
gctcagagca gattgacttg attctagagg aactttcata tattgatcaa gagaagcaag      60
ctagcttcgg tgagatcttt caaggaaaat gtcttaaagc aatgataatt ggatgtggtt     120
tggtgttctt tcagcaggtc actggtcaac ctagcgttct atactatgct gctacaattt     180
ttcagagtgc tggattctct ggggcatctg atgccactcg tgtgncaatt cttcttggct     240
tactgaagct aatcatgacc ggagtagcag tccntgggtc dacagacttg gcaggaganc     300
cattgcttat nggaggngtc agtggnatta ctg                                  333
```

<210> SEQ ID NO 24
<211> LENGTH: 346
<212> TYPE: DNA
<213> ORGANISM: Zea mays
<220> FEATURE:
<221> NAME/KEY: misc_feature
<222> LOCATION: (1)...(346)
<223> OTHER INFORMATION: n = A,T,C or G

<400> SEQUENCE: 24

```
gctacctact actcaagtat ccatccttat tgagtacagt gttgatccat ggactcggaa      60
ggagttgtag cagcaaaggt ggcagatgag actactaaac cggcaatcca agaagacggc     120
gccgagagca aggccgggat gactgatctg ctgatgctga ccgacaagtc gcagctgcag     180
gcgctggcga tgctgctgcg gaacaacgag gagctcatga tgagccaggc gatcaagtcg     240
gagacggaag cgcattgagt acctcaagac ggtgagcgac tgctacacgc ggangatgaa     300
gctcctcgac gattccatgg cggccaggac cacgtacgan cgttcg                    346
```

<210> SEQ ID NO 25
<211> LENGTH: 446
<212> TYPE: DNA

<213> ORGANISM: Zea mays
<220> FEATURE:
<221> NAME/KEY: misc_feature
<222> LOCATION: (1)...(446)
<223> OTHER INFORMATION: n = A,T,C or G

<400> SEQUENCE: 25

```
gcctccgnng cttcttccct ccctcaaatc aggaaaccat ccaacttgtc gatcggcctt      60
gcttgccttg gtactcctgc ttccgccatg gttcagatca aagagttgta tcctccccca    120
ttccaagttc ttgtgtcagc agtgtttaat tctggtaccc gcgtttgaat tttgctgtat    180
atattatttg cgcgtatacc ttgactcgaa tctcgcgcga cgtacgaaag ccggatcgtc    240
atgcccatgt ccatggaaga gtacgagata gggctgagct acaccatcat gaagatggag    300
cagcagaaca ccaacagcaa ggagggcgtg gaggtgctgc agcaggcccc gttccacgag    360
gatgccaagc ttggcaaggg ccacttcact tccaaagttt atcatctgca aagcaagatt    420
ccgtcatgga tgaagggctt tcacct                                         446
```

<210> SEQ ID NO 26
<211> LENGTH: 549
<212> TYPE: DNA
<213> ORGANISM: Zea mays
<220> FEATURE:
<221> NAME/KEY: misc_feature
<222> LOCATION: (1)...(549)
<223> OTHER INFORMATION: n = A,T,C or G

<400> SEQUENCE: 26

```
ggcacgagca aggtggttgc acaccagagc tctgcttctc ggatgatgat tttgatatgg     60
tacctgattg ccaccggaaa cctctgatta gacttggtgc acacatgcca gcccgggcag    120
agcaagcatc caggaggagt gaattcgacc cgcttctcct aacaggcggt ggattcctgt    180
tcccaaacca gaccggcgaa tgcatgatgt gatcctattc tttgggataa tcgacatcct    240
ccaggattac agcttaagaa agcgggccga gcatgcttac aagtcattac agacagatcc    300
caactcgatc tctgccgtgg acccgaagct ctactcgaag agtttccaag acttccatcg    360
ggcagaattt ttgtggaaat ggctaanngg cntggatagn nttaaccgcg aattccatgg    420
cggaggccag agcacntgtn aaggattccg tgggcatttt tttgcgcgca tnaagaatct    480
anctaatgcc agaatcatct tcatccnggg gatcngtaaa cagcaccggt gggaactact    540
gtgaagcnt                                                            549
```

<210> SEQ ID NO 27
<211> LENGTH: 434
<212> TYPE: DNA
<213> ORGANISM: Zea mays
<220> FEATURE:
<221> NAME/KEY: misc_feature
<222> LOCATION: (1)...(434)
<223> OTHER INFORMATION: n = A,T,C or G

<400> SEQUENCE: 27

```
ccacgcgtcc gcggnacgct ggcgtnccaa atggggaagt atttgacccc aaggctagtt     60
tgccagtgaa gaaacccctc aaggtgaaag tatatatggg agacgggtgg ngccatggac    120
ttcagtaaaa ctcatttcga tgccttttcg cctccagatt tctatactag ggtagggatc    180
gcaggtgtga aggcagacag tgtgatgaag aagacaaggg tgattgagga ccagtgggtg    240
ccgatgtggg atgaggagtt cacgttcctt ctgaacggtt ccggagctgg ccctcctgag    300
ggtaagaagg tccaaggaat acgaacatgt cggagaagca cganccttccg ggggggcaga    360
```

```
ncagtgttgc cggtattggg agctgaagca gggcatccgt gcctgtgccc ctgcacgatc    420
gcaagggtgt aagg                                                     434

<210> SEQ ID NO 28
<211> LENGTH: 1082
<212> TYPE: DNA
<213> ORGANISM: Zea mays

<400> SEQUENCE: 28
agaattcggc acgaggttgc gggcgaaccg aaaatcacgg gcgcgagaga tcggagcacg     60
gcatgtcgga ggagcagttc ctcgccgtgg cggtggaagc cgccaagagc gccggcgaga    120
ttattcgcaa gggattctac cagaccaaga acgtcgagca aagggccag gtggatttgg     180 tgacggagac ggacaaggcc tgcgaggacc tcatcttcaa ccacctccgg aagcacttcc    240
cggaccacaa gttcatcggg gaggaggagt ccgcggcgct cggggccacc gctgacctca    300
ccgacgaccc cacctggatc gtcgatcccc tcgacgggac cactaatttc gtccatggtt    360
tcccatttgt atgtgtctcc gttggcctca ccattgggaa aattcccact gtcggagtcg    420
tcttcaaccc catcatgaac gaacttttca cggcggttcg tggaaaaggg gctttcctga    480
atggctctcc aattaaagca tcatctcaag atgagttagt gaaggctctt ctggtaacag    540
aggctggaac caatagagac aagaccactg tggatgatac aaccaacaga atcaacaggc    600
tactatacaa gattcgatcc atacggatgt gtggatcatt ggctttaaac atgtgtggag    660
ttgcctgtgg tagactagat ttgtgttatg agataggatt tggtggtcca tgggatgttg    720
ctgctggtgc tgtaattctt caggaagccg gtggccttgt ttttgaccca gcggcggag    780 agtttgattt gatgtcgcga agaatggcag gatcaaacag cttgctgaag gataagttcg    840
tcaaggaact gggggatact aattgaaaca atgttagta ttattcgtgg aacagattaa    900
gacaataagg ttgccccgcc gcatggtgat taacttattg tttgggcaac aaaattccat    960
gtaattctgc acctgtacaa ctatgttgga cgcagaacat tttattgagt tttgtgatta   1020
catgggtata cataggttga ggcaacggtc cctactttaa aaaaaaaaa aaaaaactcg   1080 ag                                                                 1082

<210> SEQ ID NO 29
<211> LENGTH: 1330
<212> TYPE: DNA
<213> ORGANISM: Zea mays

<400> SEQUENCE: 29
aggtgacact attagaagag ctatgacgtc gcatgcacgc gtacgtaagc ttggatcctc     60
tagagcggcc gcccttttt tttttttttt ttttagagga gtcgtaaagg aattttatag    120
gaatcagttt attttcacag gaaatacata ggaaatggga aaaatccca catttcaaag    180 aaggcctaaa ttggatccaa acagttggcc ttaatcaatt tgctcggcca ggtagaatag    240
tacctggtaa aggtaccaag catgccctaa cccttctgtc aatcagtatt cgccatagtt    300
caatcaattt gaaacggtgt ctccacttgg ctgctggcca cattgccggt tttgctatat    360
atatatgccc aaggcaaatc gtttctgaaa aactgataca ggaagaattc tcgcatacaa    420
actacgagca tatacacagc agaacttctg gctgctcatt caagattcag cgttgggaat    480
cttcatcggg atgtgtactg tagagtgagt tcactttrgc ayttttgwac atgttgtcaa    540
ttcacgccct tggtwgtact ttgagcagtt gcgggacgyt tcttttttgt atgtcgggkt    600
```

```
ratcaaaatc acggtccatg tcaaaacggt actggttcca rgtgcamatc ctttacgaat    660
tcaaaacctt tgagccttyt tctcttttcc tattcttgac agctctccta aaatgtattc    720
cttttgttcy tggattawtg cacaaggact cgaaaatcac macttawtcc atttgctgca    780
gcccaactyc tcgagaacct ccttgtttgg gattgaccac agcaacaaga aaggactcaa    840
agctgttccc atatatccat atcgagtcta tagcagaaac aagaccataa acattctcca    900
aattttcaac tgccacatat tcaccctgtg aaagtttgaa tatattcttt ttacggtcta    960
tgattttcat agatccatca ggttgccact caccaatgtc accagtgtgg aaccatccat   1020
caatgaggac ctcctttgta aggtcttcac gcttgtagta tcctgagaat aatgtttctc   1080
ccctgatgca tatctctcca cgaggtttgc tagcaagtgc atcataatcc atttctggga   1140
ccgactccag acgaacatcg atgtttggca ctgggggggcc aacagttcct atcatggaca   1200
tttgatttgg tagcgagacg aaagatccag cacaagtttc cgcggacgcg tgggtcgacc   1260
cgggaattcc ggaccggtac ctgcaggcgt accagctttc cctatagtga gtcgtattag   1320
agctttggcg                                                          1330
```

<210> SEQ ID NO 30
<211> LENGTH: 720
<212> TYPE: DNA
<213> ORGANISM: Zea mays
<220> FEATURE:
<221> NAME/KEY: misc_feature
<222> LOCATION: (1)...(720)
<223> OTHER INFORMATION: n = A,T,C or G

<400> SEQUENCE: 30

```
gcagacggaa tgaagacttt gaccatgtct ttagatcaat gacatttct tctccttcaa      60 atggattatt gacaacatca gtttctggtt ctgctgctca gcttcttcga ggaacaaatg    120
gatcaagact gcctgagttg tcagatactg acttgatcgt gtttcttggt gacttcaatt    180
accggcttta taacatttct ttcgatgagg caatgggctt ggtttcccgg cgatgctttg    240
actggttgag agagaatgat cagctgcgag cagaaatgaa atctgggaga gtcttccagg    300
gattacgtga aggagaattt aagttccccc ctacttataa atttgagaag cacatagcan    360
gcttatctgg ttatgataat agtgagaaaa ggcgcattcc aagcctggtg tgacagagtt    420
ctatatcgag acagccgaac tagttcacag attgagtgtt ctttggaatg tcctgtagtc    480
tgttcgatat cactgtacga ctcttgtatg gaagcaacag acagtgatca taaacctgtc    540
aaatgtgtgt tcaatttaga tattgctcat gtggacaaaa caaaacaatg angcaaaant    600
atggagaaat aatgggttca aataaaggaa tgcntgactc acttcaaggc cttggaggct    660
ttgcctgaan tagatatcaa cacgaatgac atcantccgc aagatnaaaa nccntttgtg    720
```

<210> SEQ ID NO 31
<211> LENGTH: 1255
<212> TYPE: DNA
<213> ORGANISM: Zea mays

<400> SEQUENCE: 31

```
ccgggtcgac ccacgcgtcc gcggacgcgt gggcccttta cacgctcgat tcccccgcc      60 gtttccacgg gggccaggtg cctgcattac tgggtccggg cctagcgtca gcgcaaccga    120
acacgccggc gaccgctgcc gcccttctcc cagctgccca ggtcttcgtc gggccctttg    180
cctgcggcgt cggcgacgag cgcctgccac accagggtat tttaggatca tcataaattt    240
cattgcattt gcggtttgct attccaacaa ggctctcttt gctatcctgt acttcatcag    300
```

-continued

```
ctttgtcctt gatggtgtgg atggttggtt tgcaaggaag ttcaatcaag catcaacctt      360
tggagctgtg ttagacatgg ttacagatag ggttagcact gcttgtttgt tggcccttct      420
ctcccagttt tacagacytg gtttagtctt tcttgatatt gctttggatt ggwtattacg      480
agccactggt ttcaaatkka cmagttcttt tctttgtcag gtargactta gccacaaggw      540
tgtaaaacac acaggcaatt ggcttctgaa attatattat gggtacaggc cattcatgsc      600
cttctgctgt gttycttgtr aggtttwata tawtttccyg tttctctttg ctgawgarga      660
gtcaacaarc cttgcttagt gtatgcaaaa ggmatcctga accaaartcc cgttcgttaw      720
cytggkgttk gtttcmacyc wagttggctg ggcagtgaag caagccacca acgtcatcca      780
gatgaaaact gctgcggacg catgcgtggt gtatgatctg aagcgcagca aatgaagcat      840
gaaggcagct tcacggttta gtatcgacat atccaaggga aaactctgcg aggggcggg      900 ctacgtcttg cgtgccttga catctttctg atgatgcggt catatgtggg accaggggat      960
gacatgccgt ggccaatgca aacaattgtt ttgtgaaagc agcggccgtt aagttgttgt     1020
cagtgtgaga gtggtgatgc gatcatgatc cttttacct agagtagctc ccctttgtgt      1080
tagcctgaac gatgtttgc aagccgcatg ttccgaactc taggattatt tggattacaa     1140
aacttacata ttccatcctc aaaaaaaaaa aaaagggcg gccgctctag aggatccaag     1200
cttacgtacg cgtgcatgcg acgtcatagc tcttctatag tgtcacctaa attca         1255
```

GENES CONTROLLING PHYTATE METABOLISM IN PLANTS AND USES THEREOF

This application is a divisional of application Ser. No. 09/118,442 filed Jul. 17, 1998, U.S. Pat. No. 6,197,561, the disclosure of which is herein incorporated by reference.

FIELD OF THE INVENTION

The present invention relates to the field of animal nutrition. Specifically, the present invention relates to the identification and use of genes encoding various enzymes involved in the metabolism of phytate in plants and the use of these genes and mutants thereof to reduce the levels of phytate, and/or increase the levels of non-phytate phosphorus in food or feed.

BACKGROUND OF THE INVENTION

The role of phosphorus in animal nutrition is well recognized. Eighty percent of the phosphorus in the body of animals is found in the skeleton, providing structure to the animal. Twenty percent of the phosphorus in animals can be found in soft tissues, where it is a constituent compound and therefore involved in a wide series of biochemical reactions. For example, phosphorus is required for the synthesis and activity of DNA, RNA, phospholipids, and some B vitamins.

Though phosphorus is essential for healthy animals, it is also recognized that not all phosphorus in feed is bioavailable. Phytic acid salts (i.e., phytates) are the major storage form of phosphorus in plants. See e.g., "Chemistry and Application of Phytic Acid: an Overview," *Phytic Acid: Chemistry and Application;* Graf, Ed.; Pilatus Press: Minneapolis, Minn., pp. 1–21; (1986). Phytates are the major form of phosphorus in seeds, typically representing from 50% to 80% of seed total phosphorus.

In corn and soybeans, for example, phytate represents about 60% to 80% of total phosphorus. When seed-based diets are consumed by non-ruminants, the consumed phytic acid forms salts with several nutritionally-important minerals in the intestinal tract. Excretion of these salts reduces the retention and utilization, i.e., bioavailability of the diet's phosphorus and mineral contents. Consequently, this can result in mineral deficiencies in both humans and animals fed the above seed. See e.g., McCance, et al., *Biochem. J.,* 29:4269 (1935); Edman, *Cereal Chem.,* 58:21 (1981).

Phytate, a large source of phosphorus, is not metabolized by monogastric animals. Phytic acid, in fact, is considered to be an anti-nutritional factor because it reduces the bioavailability of proteins and minerals by chelation; see e.g., Cheryan, "Phytic Acid Interactions in Food Systems," *CRC Crit. Rev. Food Sci. Nutr.,* 13:297–335 (1980).

Phytate does not simply cause a reduction in nutrient availability. The phytate-bound phosphorus in animal waste contributes to surface and ground water pollution. See e.g., Jongbloed, et al., *Nether. J. Ag. Sci.* 38:567 (1990).

Because the phytate content of seed has an impact on diet, phosphorus and mineral retention, and the environment, several approaches have been proposed to reduce this impact. Approaches include removing dietary phytate by post-harvest intervention and reducing seed phytate content genetically.

Post-harvest food processing methods that remove phytic acid either physically or via fermentation, are disclosed for example by lndumadhavi, et al., *Int. J. Food Sci. Tech.* 27:221 (1992). Hydrolyzing phytic acid is a useful approach to increase the nutritional value of many plant foodstuffs. Phytases, as discussed more fully below, catalyze the conversion of phytic acid to inositol and inorganic phosphate. Phytase-producing microorganisms include bacteria and yeasts. See e.g. Power, et al, *J. Bacteriol.* 151:1102–1108 (1982); Segueilha, et al., Biotechnol. Lett. 15(4):399–404 (1993) and Nayini, et al., *Lebensm. Wiss. Technol.* 17:24–26 (1984).

The use of phytases, phytic acid-specific phosphohydrolases, typically of microbial origin, as dietary supplements, is disclosed by Nelson, et al., *J. Nutr.* 101:1289 (1971). All currently known post-harvest technologies involve added procedures and expense in order to circumvent problems associated with phytate.

The genetic approach involves developing crop germplasm possessing heritable reductions in seed phytic acid. Heritable quantitative variation in seed phytic acid has been observed among lines of several crop species. See Raboy, In: *Inositol Metabolism in Plants,* Moore D. J., et al., (eds.) Alan R. Liss, New York, pp. 52–73; (1990).

However, this variation has been found to be highly and positively correlated with variation in less desirable characteristics, therefore, breeding for reduced seed phytic acid using traditional breeding methods, could result in germplasm with undesirable correlated characteristics. To date, there have been no reports of commercially acceptable low phytic acid corn germplasm produced by such an approach.

In genetically altering phytate, natural variability for phytate and free phosphorus has been examined. See Raboy, V. and D. B. Dickinson *Crop Sci.* 33:1300–1305 (1993), and Raboy, V. et al., Maydica 35:383–390(1990). While some variability for phytic acid was observed, there was no corresponding change in non-phytate phosphorus. In addition, varietal variability represented only two percent of the variation observed, whereas ninety-eight percent of the variation in phytate was attributed to environmental factors.

As mentioned above, studies of soybean and other crops have indicated that altering genetic expression of phytate through recurrent selection breeding methods might have correlated undesirable results. See Raboy, V., D. B. Dickinson, and F. E. Below; *Crop Sci.* 24:431–434 (1984); Raboy, V., F. E. Below, and D. B. Dickinson; *J. Hered.* 80:311–315 (1989); Raboy, V., M. M. Noaman, G. A. Taylor, and S. G. Pickett; *Crop Sci.* 31:631–635; (1991).

While it has been proposed that a block in phytic acid accumulation might be valuable in producing low phytic acid germplasm without the introduction of undesirable correlated responses, (See Raboy, et al., *Crop Sci.* 33:1300 (1993)) employing such a traditional mutant selection approach has, in certain cases, revealed that homozygosity for mutants associated with substantial reductions in phytic acid also proved to be lethal.

Myo-inositol is produced from glucose in three steps involving the enzymes hexokinase (EC 2.7.1.1), L-myo-inositol 1-phosphate synthase (EC 5.5.1.4) and L-myo-inositol 1-phosphate phosphatase (EC 3.1.3.25). The biosynthetic route leading to phytate is complex and not completely understood. Without wishing to be bound by any particular theory of the formation of phytate, it is believed that the synthesis may be mediated by a series of one or more ADP-phosphotransferases, ATP-dependent kinases and isomerases. A number of intermediates have been isolated including for example 2 and 3 monophosphates, 1,3 and 2,6 di-phosphates, 1,3,5 and 2,5,6 triphosphates, 1,3,5,6 and 2,3,5,6 tetra-phosphates, and 1,2,4,5,6 and 1,2,3,4,6 pentaphosphates. Several futile cycles of dephosphorylation and rephosphorylation of the $P_5$ and $P_6$ forms have been reported as well as a cycle involving G6P→myoinositiol-1-phosphate→myo-inositol; the last step being completely reversible, indicating that control of metabolic flux through this pathway may be important. This invention differs from the foregoing approaches in that it provides tools and reagents that allows the skilled artisan, by the application of, inter alia, transgenic methodologies to influence the metabolic flux in respect to the phytic acid pathway. This influence may be either anabolic or catabolic, by which is meant the influence may act to decrease the flow resulting from the biosynthesis of phytic acid and/or increase the degradation (i.e., catabolism of phytic acid). A combination of both approaches is also contemplated by this invention.

As mentioned above, once formed phytate may be dephosphorylated by phosphohydrolases, particularly 3-phytases typically found in microorganisms and 6-phytases the dominant form in plants. After the initial event, both enzymes are capable of successive dephosphorylation of phytate to free inositol.

Accordingly, there have also been reports that plants can be transformed with constructs comprising a gene encoding phytase. See Pen, et al, PCT Publication WO 91/14782, incorporated herein in its entirety by reference. Transgenic seed or plant tissues expressing phytases can then be used as dietary supplements. However, this application has not been done to reduce seed phytic acid.

Based on the foregoing, there exists the need to improve the nutritional content of plants, particularly corn and soybean by increasing non-phytate phosphorus and reducing seed phytate with no other obvious or substantial adverse effects.

SUMMARY OF THE INVENTION

It is therefore an object of the present invention to provide plants, particularly transgenic corn, which has enhanced levels of non-phytate phosphorus without corresponding detrimental effects.

It is a further object of the present invention to provide plants, particularly transgenic corn which have reduced levels of phosphorus in the form of phytate without corresponding detrimental effects.

It is a further object of the present invention to provide transgenic plant lines with dominant, heritable phenotypes which are useful in breeding programs designed to produce commercial products with improved phosphorus availability and reduced phytate.

It is a further object of the present invention to improve animal performance by feeding animals plants and parts thereof particularly seeds with enhanced nutritional value.

It is a further object of the present invention to provide plant seeds, particularly corn seeds and resulting meal, that result in less environmental contamination, when excreted, than do currently used seeds.

These and other objects of the invention will become readily apparent from the ensuing description.

An isolated polynucleotide is provided comprising a member selected from the group consisting of:
(a) a polynucleotide encoding a polypeptide comprising SEQ ID NOS: 2, 6, 11, 17 or complement thereof;
(b) a polynucleotide of at least 25 nucleotides in length which selectively hybridizes under stringent conditions to a polynucleotide of SEQ ID NOS: 1, 5, 7, 10, 14, 15, 16 or a complement thereof, wherein the hybridization conditions include a wash step in 0.1×SSC at 60° C.;
(c) a polynucleotide having a sequence of a nucleic acid amplified from a *Zea mays* nucleic acid library using the primers of SEQ ID NOS: 3–4, 8–9, 12–13, or 18–19;
(d) a polynucleotide having at least 75% sequence identity to SEQ ID NO: 1, at least 60% sequence identity to SEQ ID NO: 5, at least 80% sequence identity to SEQ ID NO: 10, or at least 70% sequence identity to SEQ ID NO: 16, wherein the % sequence identity is based on the entire coding region and is determined by the GAP program where the gap creation penalty=50 and the gap extension penalty=3; and
(e) a polynucleotide comprising at least 20 contiguous bases of the polynucleotide of (a) through (c), or complement thereof.

According to the present invention, polypeptides that have been identified as novel phytate biosynthetic enzymes are provided.

An isolated polypeptide is provided comprising an amino acid sequence which has at least 80% sequence identity to SEQ ID NO: 2, at least 35% sequence identity to SEQ ID NO: 6, at least 90% sequence identity to SEQ ID NO: 11 or at least 80% sequence identity to SEQ ID NO: 17, wherein the % sequence identity is based on the entire sequence and is determined by the GAP program where the gap creation penalty=12 and the gap extension penalty=4.

It is a further object of the invention, moreover, to provide polynucleotides that encode maize phytate biosynthetic enzymes, particularly polynucleotides that encode phosphatidylinositol 3-kinase, myo-inositol, monophosphatase-3, myo-inositol 1,3,4-triphosphate 5/6 kinase and myo-inositol 1-phosphate synthase.

In a particularly preferred embodiment of this aspect of the invention the polynucleotide comprises the regions encoding phosphatidylinositol 3-kinase, myo-inositol monophosphatase-3, myo-inositol 1,3,4-triphosphate 5/6 kinase and myo-inositol 1-phosphate synthase.

In another particularly preferred embodiment of the present invention polypeptides are isolated from *Zea mays*.

In accordance with this aspect of the present invention there is provided a polynucleotide of at least 25 nucleotides in length which selectively hybridizes under stringent conditions to the polynucleotides set out below, or a complement thereof. As used herein, "stringent conditions" means the hybridization conditions include a wash step in 0.1×SSC at 60° C.

In accordance with this aspect of the present invention there is provided a polynucleotide having a sequence of a nucleic acid amplified from a *Zea mays* nucleic acid library using the primers set out in the sequences below.

In accordance with this aspect of the invention there are provided isolated nucleic acid molecules encoding phytate biosynthetic enzymes, particularly those from *Zea mays*, mRNAs, cDNAs, genomic DNAs and, in further embodiments of this aspect of the invention, biologically, useful variants, analogs or derivatives thereof, or fragments thereof, including fragments of the variants, analogs and derivatives.

Other embodiments of the invention are naturally occurring allelic variants of the nucleic acid molecules in the sequences provided which encode phytate biosynthetic enzymes.

In accordance with another aspect of the invention there are provided novel polypeptides which comprise phytate biosynthetic enzymes of maize origin as well as biologically, or diagnostically useful fragments thereof, as well as variants, derivatives and analogs of the foregoing and fragments thereof.

It also is an object of the invention to provide phytate biosynthetic polypeptides, particularly phosphatidylinositol 3-kinase, myo-inositol monophosphatase-3, myo-inositol 1,3,4-triphosphate 5/6 kinase or myo-inositol 1-phosphate synthase polypeptide, that may be employed for modulation of phytic acid synthesis.

In accordance with yet a further aspect of the present invention, there is provided the use of a polypeptide of the invention, or particular fragments thereof.

It is another object of the invention to provide a process for producing the polypeptides, polypeptide fragments, variants and derivatives, fragments of the variants and derivatives, and analogs of the foregoing.

In a preferred embodiment of this aspect of the invention there are provided methods for producing the polypeptides comprising culturing host cells having expressibly incorporated therein a polynucleotide under conditions for expression of phytate biosynthetic enzymes in the host and then recovering the expressed polypeptide.

In accordance with another object of the invention there are provided products, compositions, processes and methods that utilize the aforementioned polypeptides and polynucleotides, for purposes including research, biological, and agricultural.

In accordance with yet another aspect of the present invention, there are provided inhibitors to such polypeptides, useful for modulating the activity and/or expression of the polypeptides. In particular, there are provided antibodies against such polypeptides.

In accordance with certain embodiments of the invention there are probes that hybridize to phytate biosynthetic enzyme polynucleotide sequences useful as molecular markers in breeding programs.

In certain additional preferred embodiments of this aspect of the invention there are provided antibodies against the phytate biosynthetic enzymes. In certain particularly preferred embodiments in this regard, the antibodies are selective for the entire class the phytate biosynthetic enzymes, irrespective of species of origin as well as species-specific antibodies, such as antibodies capable of specific immune reactivity with for example, Zea mays phytate biosynthetic enzymes.

In accordance with yet another aspect of the present invention, there are provided phytate enzyme antagonists. Among preferred antagonists are those which bind to phytate biosynthetic enzymes so as to inhibit the binding of binding molecules or to stabilize the complex formed between the phytate biosynthetic enzyme and the binding molecule to prevent further biological activity arising from the phytate biosynthetic enzyme. Also among preferred antagonists are molecules that bind to or interact with phytate biosynthetic enzymes so as to inhibit one or more effects of a particular phytate biosynthetic enzyme or which prevent expression of the enzyme and which also preferably result in a lowering of phytic acid accumulation.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE INVENTION

This invention relates, in part, to newly identified polynucleotides and polypeptides; variants and derivatives of these polynucleotides and polypeptides; processes for making these polynucleotides and these polypeptides, and their variants and derivatives and antagonists of the polypeptides; and uses of these polynucleotides, polypeptides, variants, derivatives and antagonists. In particular, in these and in other regards, the invention relates to polynucleotides and polypeptides of the phytate metabolic pathway, most particularly with the enzymes phosphatidylinositol 3-kinase, myo-inositol monophosphatase-3, myo-inositol 1,3,4-triphosphate 5/6 kinase and myo-inositol 1-phosphate synthase and genes encoding same.

Glossary

The following illustrative explanations are provided to facilitate understanding of certain terms used frequently herein, particularly in the Examples. The explanations are provided as a convenience and are not limitative of the invention.

PHYTATE BIOSYNTHETIC ENZYME-BINDING MOLECULE, as used herein, refers to molecules or ions which bind or interact specifically with phytate biosynthetic enzyme polypeptides or polynucleotides of the present invention, including, for example enzyme substrates, cell membrane components and classical receptors. Binding between polypeptides of the invention and such molecules, including binding or interaction molecules may be exclusive to polypeptides of the invention, which is preferred, or it may be highly specific for polypeptides of the invention, which is also preferred, or it may be highly specific to a group of proteins that includes polypeptides of the invention, which is preferred, or it may be specific to several groups of proteins at least one of which includes a polypeptide of the invention. Binding molecules also include antibodies and antibody-derived reagents that bind specifically to polypeptides of the invention.

GENETIC ELEMENT, as used herein, generally means a polynucleotide comprising a region that encodes a polypeptide or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

HOST CELL, as used herein, is a cell which has been transformed or transfected, or is capable of transformation or transfection by an exogenous polynucleotide sequence. Exogenous polynucleotide sequence is defined to mean a sequence not naturally in the cell. This includes transformation to incorporate additional copies of an endogenous polynucleotide.

IDENTITY and SIMILARITY, as used herein, and as known in the art, are relationships between two polypeptide sequences or two polynucleotide sequences, as determined by comparing the sequences. In the art, identity also means the degree of sequence relatedness between two polypeptide or two polynucleotide sequences as determined by the match between two strings of such sequences. Both identity and similarity can be readily calculated (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). Methods commonly employed to determine identity or similarity between two sequences include, but are not limited to those disclosed in Carillo, H., and Lipman, D., SIAM *J. Applied Math.,* 48:1073 (1988). Preferred methods to determine identity are designed to give the largest match between the two sequences tested. Methods to determine identity and similarity are codified in computer programs. Typical computer program methods to determine identity and similarity between two sequences include, GCG program package (Devereux, J., et al., *Nucleic Acids Research* 12(1):387 (1984)), BLASTP, BLASTN, FASTA and TFASTA (Atschul, S. F. et al., *J. Mol. Biol.* 215:403 (1990)).

For purposes of defining the present invention, the Gap program is used. The algorithm used for the Gap program is that of Needleman and Wunsch (*J. Mol. Biol.* 48:443–453 [1970]). The parameters used are as follows: for nucleotide comparisons the gap creation penalty=50, gap extension penalty=3; for amino acid comparisons the gap creation penalty=12, the gap extension penalty=4.

ISOLATED, as used herein, means altered "by the hand of man" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the tern is employed herein. For example, with respect to polynucleotides, the term isolated means that it is separated from the chromosome and cell in which it naturally occurs. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION, as used herein, refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., *MOLECULAR CLONING, A LABORATORY MANUAL,* 2nd Ed.; Cold Spring Harbor Laboratory Press, Cold Spring Harbor, N.Y. (1989) and Maniatis et al., pg. 146, as cited below.

OLIGONUCLEOTIDE(S), as used herein, refers to short polynucleotides. Often the term refers to single-stranded deoxyribonucleotides, but it can refer as well to single- or double-stranded ribonucleotides, RNA:DNA hybrids and double-stranded DNAs, among others. Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms. Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP. The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLANT, as used herein, includes, but is not limited to plant cells, plant tissue and plant seeds.

PLASMIDS, as used herein, generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S), as used herein, generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *PROTEINS—STRUCTURE AND MOLECULAR PROPERTIES,* 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in *POSTTRANSLATIONAL COVALENT MODIFICATION OF PROTEINS,* B. C. Johnson, Ed., Academic Press, New York (1983); Seifter et al., *Meth. Enzymol.* 182:626–646 (1990) and Rattan et al, *Protein Synthesis: Posttranslational Modifications and Aging, Ann. N.Y. Acad. Sci.* 663:48–62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides ma y be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionine-less amino terminal variants of the protein of the invention. The modifications that occur in a polypeptide often will be a function of how it is made. For polypeptides made by expressing a cloned gene in a host, for instance, the nature and extent of the modifications in large part will be determined by the host cell post-translational modification capacity and the modification signals present in the polypeptide amino acid sequence. For instance, as is well known, glycosylation often does not occur in bacterial hosts such as, for example, *E. coli.* Accordingly, when glycosylation is desired, a polypeptide should be expressed in a glycosylating host, generally a eukaryotic cell. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized by expressing a polynucleotide in a host cell.

TRANSFORMATION, as used herein, is the process by which a cell is "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to higher eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA.

VARIANT(S), as used herein, of polynucleotides or polypeptides, as the term is used herein, are polynucleotides or polypeptides that differ from a reference polynucleotide or polypeptide, respectively. Variants in this sense are described below and elsewhere in the present disclosure in greater detail. With reference to polynucleotides, generally, differences are limited such that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. With reference to polypeptides generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination.

GERMPLASM, as used herein, means a set of genetic entities which may be used in a conventional breeding program to develop new plant varieties.

HIGH PHOSPHOROUS TRANSGENIC, as used herein, means an entity which, as a result of recombinant genetic manipulation, produces seed with a heritable decrease in phytic acid percentage and/or increase in non-phytate phosphorous percentage.

PHYTIC ACID, as used herein, means myo-inositol tetraphosphoric acid, myo-inositol pentaphosphoric acid and myo-inositol hexaphosphoric acid. As a salt with cations, phytic acid is "phytate".

NON-PHYTATE PHOSPHOROUS, as used herein, means total phosphorus minus phytate phosphorous.

NON-RUMINANT ANIMAL means an animal with a simple stomach divided into the esophageal, cardia, fundus and pylorus regions. A non-ruminant animal additionally implies a species of animal without a functional rumen. A rumen is a section of the digestive system where feedstuff/food is soaked and subjected to digestion by microorganisms before passing on through the digestive tract. This phenomenon does not occur in a non-ruminant animal. The term non-ruminant animal includes but is not limited to humans, swine, poultry, cats and dogs.

As mentioned above, the present invention relates to novel phytic acid metabolic polypeptides and polynucleotides encoding same, among other things, as described in greater detail below. Among the polypeptides particularly useful for the practice of this invention include but are not limited to D-myo-inositol-3-phosphate synthase, myo-inositol 1-phosphate synthase (otherwise referred to as INO1), phosphatidylinositol-4-phosphate-5-kinase, signaling inositol polyphosphate-5-phosphatase(SIP-110), myo-inositol monophosphatase-3, myo-inositol 1,3,4 triphosphate 5/6 kinase, 1D-myo-inositol trisphosphate 3-kinase B, myo-inositol monophosphatase-1, inositol polyphosphate 5-phosphatase, 1D-myo-inositol trisphosphate 3-kinase, phosphatidylinositol 3-kinase, phosphatidylinositol 4-kinase, phosphatidylinositol synthase, phosphatidylinositol transfer protein, phosphatidylinositol 4,5-bisphosphate 5-phosphatase, myo-inositol transporter, phosphatidylinositol-specific phospholipase C and maize phytase.

The nucleic acids and fragments thereof encoding the above-mentioned enzymes are useful to generate enzyme deficient transgenics. For example, a single gene or gene fragment (or combinations of several genes) may be incorporated into an appropriate expression cassette (using for example the globulin-1 promoter for embryo-preferred expression or the native promoter associated with the enzyme encoding gene) and transformed into corn along with an appropriate selectable marker (such as the herbicide PAT) in such a manner as to silence the expression of the endogenous genes.

Relevant literature describing the application of homology-dependent gene silencing include: Jorgensen, *Trends Biotechnol* 8 (12):340–344 (1990); Flavell, Proc. Nat'l. Acad. Sci. (USA) 91:3490–3496 (1994); Finnegan et al., *Bio/Technology* 12: 883–888 (1994); Neuhuber et al., *Mol. Gen. Genet.* 244:230–241 (1994). Alternatively, another approach to gene silencing can be with the use of antisense technology (Rothstein et al. in Osf. Surv. *Plant Mol. Cell. Biol.* 6:221–246 (1989).

In particular, the invention relates to polypeptides and polynucleotides of novel phytate biosynthetic enzyme genes. The invention relates especially to *Zea mays* phytate biosynthetic enzymes having the nucleotide and amino acid sequences set out below respectively.

Polynucleotides

In accordance with one aspect of the present invention, there are provided isolated polynucleotides which encode the phytate biosynthetic enzymes having the deduced amino acid sequence below.

Using the information provided herein, such as the polynucleotide sequences set out below, a polynucleotide of the present invention encoding phytate biosynthetic enzyme polypeptides may be obtained using standard cloning and screening procedures. To obtain the polynucleotide encoding the protein using the DNA sequences given below, oligonucleotide primers can be synthesized that are complementary to the known polynucleotide sequence. These primers can then be used in PCR to amplify the polynucleotide from template derived from mRNA or genomic DNA isolated from plant material. The resulting amplified products can then be cloned into commercially available cloning vectors, such as the TA series of vectors from InVitrogen. By sequencing the individual clones thus identified with sequencing primers designed from the original sequence, it is then possible to extend the sequence in both directions to determine the full gene sequence. Such sequencing is performed using denatured double stranded DNA prepared from a plasmid clone. Suitable techniques are described by Maniatis, T., Fritsch, E. F. and Sambrook, J. in MOLECULAR CLONING, A Laboratory Manual (2nd edition 1989 Cold Spring Harbor Laboratory. See Sequencing Denatured Double-Stranded DNA Templates 13.70). Illustrative of the invention, the polynucleotide set out below were assembled from a cDNA library derived for example, from germinating maize seeds.

Myo-inositol 1-phosphate synthase of the present invention is structurally related to other proteins of the myo-inositol 1-phosphate synthase family, as shown by comparing the present sequence encoding myo-inositol 1-phosphate synthase with sequences reported in the literature. A preferred DNA sequence is set out below. It contains an open reading frame encoding a protein of about 510 amino acid residues with a deduced molecular weight of about 59.7 (Calculated as the number of amino acid residues×117) kDa. The protein exhibits greatest homology to myo-inositol-1-phosphate synthase. The present myo-inositol 1-phosphate synthase has about 88% identity and about 92% similarity with the amino acid sequence of myo-inositol-1-phosphate synthase from *Mesembryantherum crystallium* and 78.7% identity at the nucleic acid level (These percentages are based on comparison of full-length coding sequence only i.e., ATG through stop codon).

Myo-inositol monophosphatase-3 of the invention is structurally related to other proteins of the myo-inositol monophosphatase-3 family, as shown by comparing the present sequence encoding myo-inositol monophosphatase-3 with that of sequence reported in the literature. A preferred DNA sequence is set out below. It contains an open reading frame encoding a protein of about 267 amino acid residues with a deduced molecular weight of about 31.2 kDa (calculated as the number of amino acid residues×117). Novel myo-inositol monophosphatase-3 identified by homology between the amino acid sequence set out below and known amino acid sequences of other proteins such as myo-inositol monophosphatase-3 from *Lycopersicum esulentum* with 76.1% identity/81.1% similarity at the amino acid level and 67.9% identity at the nucleic acid level. (These percentages are based on comparison of full-length coding sequence only i.e., ATG through stop codon).

Myo-inositol 1,3,4-trisphosphate 5/6-kinase of the invention is structurally related to other proteins of the myo-inositol 1,3,4-trisphosphate 5/6-kinase family, as shown by comparing the sequence encoding the present inositol 1,3,4-trisphosphate 5/6-kinase with that of sequence reported in the literature. A preferred DNA sequence is set out below. It contains an open reading frame encoding a protein of about 353 amino acid residues with a deduced molecular weight of about 41.3 kDa (calculated as the number of amino acid residues×117). The protein exhibits greatest homology to myo-inositol 1,3,4-trisphosphate 5/6-kinase from *Homo sapiens*. myo-inositol 1,3,4-trisphosphate 5/6-kinase below has about 34% identity and about 43.4% similarity with the amino acid sequence of myo-inositol 1,3,4-trisphosphate5/6-kinase from *Homo sapiens*. (The percentages disclosed above are based on comparison of full-length coding sequence only i.e., ATG through stop codon.)

A preferred phosphatidylinositol 3-kinase sequence is set out below. It contains an open reading frame encoding a protein of about 803 amino acid residues with a deduced molecular weight of about 94.1 kDa (calculated as the number of amino acid residues×117). The protein exhibits greatest homology to phosphatidylinositol 3-kinase from *Glycine max*. Homology between amino acid sequences set out in the following sequences and known amino acid sequences of other proteins such as phosphatidylinositol 3-kinase from *Glycine max* with 78% identity/84% similarity at the amino acid level and 73% identity at the nucleic acid level (these percentages are based on comparison of full-length coding sequence only i.e., ATG through stop codon) based on the Gap program defined below.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the antisense strand.

The coding sequence which encodes the polypeptide may be identical to the coding sequence of the polynucleotides shown below. It also may be a polynucleotide with a different sequence, which, as a result of the redundancy (degeneracy) of the genetic code, encodes the polypeptides shown below. As discussed more fully below, these alternative coding sequences are an important source of sequences for codon optimization.

Polynucleotides of the present invention which encode the polypeptides listed below may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to non-coding 5' and 3' sequences, such as the transcribed, non-translated sequences that play a role in transcription (including termination signals, for example), ribosome binding, mRNA stability elements, and additional coding sequence which encode additional amino acids, such as those which provide additional functionalities.

The DNA may also comprise promoter regions which function to direct the transcription of the mRNA encoding phytate biosynthetic enzymes of this invention. Such promoters may be independently useful to direct the transcription of heterologous genes in recombinant expression systems. Heterologous is defined as a sequence that is not naturally occurring with the promoter sequence. While the nucleotide sequence is heterologous to the promoter sequence, it may be homologous, or native, or heterologous, or foreign to the plant host.

Furthermore, the polypeptide may be fused to a marker sequence, such as a peptide, which facilitates purification of the fused polypeptide. In certain embodiments of this aspect of the invention, the marker sequence is a hexa-histidine peptide, such as the tag provided in the pQE vector (Qiagen, Inc.) and the pET series of vectors (Novagen), among others, many of which are commercially available. As described in Gentz et al., *Proc. Nat'l. Acad. Sci., (USA)* 86:821–824 (1989), for instance, hexa-histidine provides for convenient purification of the fusion is protein. The HA tag may also be used to create fusion proteins and corresponds to an epitope derived of influenza hemagglutinin protein, which has been described by Wilson et al., *Cell* 37:767 (1984), for instance.

In accordance with the foregoing, the term "polynucleotide encoding a polypeptide" as used herein encompasses polynucleotides which include a sequence encoding a polypeptide of the present invention, particularly plant, and more particularly *Zea mays* phytate biosynthetic enzymes having the amino acid sequence set out below. The term encompasses polynucleotides that include a single continuous region or discontinuous regions encoding the polypeptide (for example, interrupted by integrated phage or insertion sequence or editing) together with additional regions, that also may contain coding arid/or non-coding sequences.

The present invention further relates to variants of the present polynucleotides which encode for fragments, analogs and derivatives of the polypeptides having the deduced amino acid sequence below. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequences set out below; variants, analogs, derivatives and fragments thereof.

Further particularly preferred in this regard are polynucleotides encoding phytate biosynthetic enzyme variants, analogs, derivatives and fragments, and variants, analogs and derivatives of the fragments, which have the amino acid sequences below in which several, a few, 1 to 10, 1 to 5, 1 to 3, 2, 1 or no amino acid residues are substituted, deleted or added, in any combination. Especially preferred among these are silent substitutions, additions and deletions, which do not alter the properties and activities of the phytate biosynthetic enzymes. Also especially preferred in this regard are conservative substitutions. Most highly preferred are polynucleotides encoding polypeptides having the amino acid sequence below, without substitutions.

Further preferred embodiments of the invention are polynucleotides that are greater than 79%, preferably at least 80%, more preferably at least 85% identical to a polynucleotide encoding myo-inositol 1-phosphate synthase polypeptide having the amino acid sequence set out below, and polynucleotides which are complementary to such polynucleotides. Among these particularly preferred polynucleotides, those with at least 90%, 95%, 98% or at least 99% are especially preferred.

Further preferred embodiments of the invention are polynucleotides that are greater than 70%, preferably at least 75%, more preferably at least 80% identical to a polynucleotide encoding myo-inositol monophosphatase-3 polypeptide having the amino acid sequence set out below, and polynucleotides which are complementary to such polynucleotides. Among these particularly preferred polynucleotides, those with at least 85%, 90%, 95%, 98% or at least 99% are especially preferred.

Further preferred embodiments of the invention are polynucleotides that are greater than 45%, preferably at least 50%, more preferably at least 55%, still more preferably at least 60% identical to a polynucleotide encoding myo-inositol 1,3,4-triphosphate 5/6-kinase polypeptide having the amino acid sequence set out below, and polynucleotides which are complementary to such polynucleotides. Among these particularly preferred polynucleotides, those with at least 65%, 70%, 75%, 80%, 85%, 90%, 95%, 98% or at least 99% are especially preferred.

Further preferred embodiments of the invention are polynucleotides that are greater than 73%, preferably at least 75%, more preferably at least 80% identical to a polynucleotide encoding phosphatidylinositol 3-kiriase polypeptide having the amino acid sequence set out below, and polynucleotides which are complementary to such polynucleotides. Among these particularly preferred polynucleotides, those with at least 85%, 90%, 95%, 98% or at least 99% are especially preferred.

Particularly preferred embodiments in this respect, moreover, are polynucleotides which encode polypeptides which retain substantially the same or even exhibit a reduction in the biological function or activity as the mature polypeptide encoded by the polynucleotides set out below.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m=81.5°$ C.+16.6 (log M)+0.41 (%GC)–0.61 (% form)–500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes,* Part I, Chapter 2 "Overview of principles of hybridization and the strategy of nucleic acid probe assays", Elsevier, New York (1993); and *Current Protocols in*

*Molecular Biology*, Chapter 2, Ausubel, et al., Eds., Greene Publishing and Wiley-Interscience, New York (1995).

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding phytate biosynthetic enzymes and to isolate cDNA and genomic clones of other genes that have a high sequence similarity to the genes. Such probes generally will comprise at least 15 bases. Preferably, such probes will have at least 30 bases and may have at least 50 bases. Particularly preferred probes will have at least 30 bases and will have 50 bases or less.

The polynucleotides and polypeptides of the present invention may be employed as research reagents and materials for discovery of high phosphorous transgenic corn plants. The polynucleotides of the invention that are oligonucleotides, derived from the sequences below may be used as PCR primers in the process herein described to determine whether or not the genes identified herein in whole or in part are transcribed in phytic acid accumulating tissue.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Polypeptides

The present invention further relates to polypeptides that have the deduced amino acid sequences below.

The invention also relates to fragments, analogs and derivatives of these polypeptides. The terms "fragment," "derivative" and "analog" when referring to the polypeptides, means a polypeptide which retains essentially the same biological function or activity as such polypeptide. Fragments derivatives and analogs that retain at least 90% of the activity of the native phytate biosynthetic enzymes are preferred. Fragments, derivatives and analogs that retain at least 95% of the activity of the native polypeptides are preferred. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptides below may be (i) one in which one or more of the amino acid residues are Substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives arid analogs are deemed to be obtained by those of ordinary skill in the art, from the teachings herein.

Among the particularly preferred embodiments of the invention in this regard are polypeptides having the amino acid sequence of phytate biosynthetic enzymes set out below, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gin, exchange of the basic residues Lys and Arg and replacements among the aromatic residues Phe, Tyr.

Further particularly preferred in this regard are variants, analogs, derivatives and fragments, and variants, analogs and derivatives, of the fragments, having the amino acid sequence below, in which several, a few, 1 to 10, 1 to 5, 1 to 3, 2, 1 or no amino acid residues are substituted, deleted or added, in any combination. Especially preferred among these are silent substitutions, additions and deletions, which do not alter the properties and activities of the phytate biosynthetic enzymes. Also especially preferred in this regard are conservative substitutions. Most highly preferred are polypeptides having the amino acid sequences below without substitutions.

The polypeptides and polynucleotides of the present invention are preferably provided in an isolated form, and preferably are purified to homogeneity.

The polypeptides of the present invention include the myo-inositol 1-phosphate synthase polypeptide (in particular the mature polypeptide) as well as polypeptides which have greater than 88% identity (92% similarity) to the polypeptide, as described above in Needleman and Wunsch, and more preferably at least 90% identity (95% similarity), still more preferably at least 95% identity (98% similarity) and most preferably at least 98% identity and also include portions of such polypeptides with such portion of the polypeptide generally containing at least 30 amino acids and more preferably at least 50 amino acids.

The polypeptides of the present invention include the myo-inositol monophosphatase-3 polypeptide (in particular the mature polypeptide) as well as polypeptides which have greater than 77% identity (82% similarity) to the polypeptide, as described above in Needleman and Wunsch, more preferably at least 80% identity (85% similarity), still more preferably at least 85% identity (90% similarity), still more preferably at least 90% identity (95% similarity), still more preferably at least 95% identity (98% similarity) and most preferably at least 98% identity and also include portions of such polypeptides with such portion of the polypeptide generally containing at least 30 amino acids and more preferably at least 50 amino acids.

The polypeptides of the present invention include the myo-inositol 1,3,4-triphosphate 5/6-kinase polypeptide (in particular the mature polypeptide) as well as polypeptides which have greater than 35% identity (45% similarity) to the polypeptide, as described above in Needleman and Wunsch, more preferably at least 50% identity (60% similarity), still more preferably at least 60% identity (70% similarity), more preferably at least 80% identity (85% similarity), still more preferably at least 70% identity (80% similarity), more preferably at least 80% identity (85% similarity), still more preferably at least 85% identity (90% similarity), still more preferably at least 90% identity (95% similarity), still more preferably at least 95% identity (98% similarity) and most preferably at least 98% identity and also include portions of such polypeptides with such portion of the polypeptide generally containing at least 30 amino acids and more preferably at least 50 amino acids.

The polypeptides of the present invention include the phosphatidylinositol 3-kinase polypeptide (in particular the mature polypeptide) as well as polypeptides which have greater than 78% identity (84% similarity) to the polypeptide, as described above in Needleman and Wunsch, more preferably at least 80% identity (85% similarity), still more preferably at least 85% identity (90% similarity), still more preferably at least 90% identity (95% similarity), still more preferably at least 95% identity (98% similarity) and most preferably at least 38% identity and also include portions of such polypeptides with such portion of the polypeptide generally containing at least 30 amino acids and more preferably at least 50 amino acids.

Vectors, Host Cells, Expression

The present invention also relates to vectors comprising the polynucleotides of the present invention, host cells that incorporate the vectors of the invention and the production of polypeptides of the invention by recombinant techniques.

Host cells can be genetically engineered to incorporate the polynucleotides and express polypeptides of the present invention. For instance, the polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, plant cells. In this case the polynucleotides generally will be stably incorporated into the host cell genome.

Alternatively, the polynucleotides may be joined to a vector containing a selectable marker for propagation in a host. The vector construct may also be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al., cited above, which is illustrative of the many laboratory manuals that detail these techniques.

Vectors

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for preferred expression. Such preferred expression may be inducible expression or expression predominantly in certain types of cells or both inducible and cell-preferred. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art. Such vectors include, among others, chromosomal, episomal and virus-derived vectors, e.g., vectors derived from bacterial plasmids, from bacteriophage, from transposons, from yeast episonles, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids and binaries used for Agrobacterium-mediated transformations. All may be used for expression in accordance with this aspect of the present invention. Generally, any vector suitable to maintain, propagate or express polynucleotides to express a polypeptide in a host may be used for expression in this regard.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Useful plant binaries vectors include BIN19 and its derivatives available from Clontech. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

In general, expression constructs will contain sites for transcription initiation and termination, and, in the transcribed region, a ribosome binding site for translation. The coding portion of the mature transcripts expressed by the constructs will include a translation initiating AUG, at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination, among others. For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Generally, recombinant expression vectors will include origins of replication, a promoter derived from a highly-expressed gene to direct transcription of a downstream structural sequence, and a selectable marker to permit isolation of vector containing cells after exposure to the vector.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers. Additional enhancers useful in the invention to increase transcription of the introduced DNA segment, include, inter alia, viral enhancers like those within the 35S promoter, as shown by Odell et al., *Plant Mol. Biol.* 10:263–72 (1988), and an enhancer from an opine gene as described by Fromm et al, *Plant Cell* 1:977(1989).

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), metallothionein promoters, such as the mouse metallothionein-I promoter and various plant promoters, such as globulin-1. When available, the native promoters of the phytate biosynthetic enzyme genes may be used.

As mentioned above, the DNA sequence in the expression vector is operatively linked to appropriate expression control sequence(s), including, for instance, a promoter to direct mRNA transcription. Representatives of prokaryotic promoters include the phage lambda PL promoter, the *E. coli* lac, trp and tac promoters to name just a few of the well-known promoters.

With respect to plants, examples of seed-specific promoters include promoters of seed storage proteins which express these proteins in seeds in a highly regulated manner (Thompson, et al.; *BioEssays;*. 10:108; (1989), incorporated herein in its entirety by reference), such as, for dicotyledonous plants, a bean β-phaseolin promoter, a napin promoter, a β-conglycinin promoter, and a soybean lectin promoter. For monocotyledonous plants, promoters useful in the practice of the invention include, but are not limited to, a maize 15 kD zein promoter, a 22 kD zein promoter, a γ-zein promoter, a waxy promoter, a shrunken 1 promoter, a globulin 1 promoter, and the shrunken 2 promoter. However, other promoters useful in the practice of the invention are known to those of skill in the art.

Other examples of suitable promoters are the promoter for the small subunit of ribulose-1,5-bis-phosphatecarboxylase, promoters from tumor-inducing plasmids of *Agrobacterium tumefaciens,* such as the nopaline synthase and octopine synthase promoters, and viral promoters such as the cauliflower mosaic virus (CaMV) 19S and 35S promoters or the figwort mosaic virus 35S promoter.

It will be understood that numerous promoters not mentioned are suitable for use in this aspect of the invention are well known and readily may be employed by those of skill in the manner illustrated by the discussion and the examples herein. For example this invention contemplates using the native phytate biosynthetic enzyme promoters to drive the expression of the enzyme in a recombinant environment.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other prokaryotes. Kanamycin and herbicide resistance genes (PAT and BAR) are generally useful in plant systems.

Selectable marker genes, in physical proximity to the introduced DNA segment, are used to allow transformed cells to be recovered by either positive genetic selection or screening. The selectable marker genes also allow for maintaining selection pressure on a transgenic plant population, to ensure that the introduced DNA segment, and its controlling promoters and enhancers, are retained by the transgenic plant.

Many of the commonly used positive selectable marker genes for plant transformation have been isolated from bacteria and code for enzymes that metabolically detoxify a selective chemical agent which may be an antibiotic or a herbicide. Other positive selection marker genes encode an altered target which is insensitive to the inhibitor.

A preferred selection marker gene for plant transformation is the BAR or PAT gene, which is used with the selecting agent bialaphos. Spencer et al., T. Thero. Appl'd Genetics 79:625–631 (1990). Another useful selection marker gene is the neomycin phosphotransferase II (nptII) gene, isolated from Tn5, which confers resistance to kanamycin when placed under the control of plant regulatory signals. Fraley et al., *Proc. Nat'l Acad. Sci.* (*USA*) 80:4803 (1983). The hygromycin phosphotransferase gene, which confers resistance to the antibiotic hygromycin, is a further example of a useful selectable marker. Vanden Elzen et al, *Plant Mol. Biol.* 5:299 (1985). Additional positive selectable markers genes of bacterial origin that confer resistance to antibiotics include gentamicin acetyl transferase, streptomycin phosphotransferase, aminoglycoside-3'-adenyl transferase and the bleomycin resistance determinant. Hayford et al., *Plant Physiol.* 86:1216 (1988); Jones et al., *Mol. Gen. Genet.* 210:86 (1987); Svab et al., *Plant Mol. Biol.* 14:197 (1990); Hille et al., *Plant Mol. Biol.* 7:171 (1986).

Other positive selectable marker genes for plant transformation are not of bacterial origin. These genes include mouse dihydrofolate reductase, plant 5-enolpyruvylshikimate-3-phosphate synthase and plant acetolactate synthase. Eichholtz et al., *Somatic Cell Mol. Genet.* 13:67 (1987); Shah et al, *Science* 233:478 (1986); Charest et al., *Plant Cell Rep.* 8:643 (1990).

Another class of useful marker genes for plant transformation with the DNA sequence requires screening of presumptively transformed plant cells rather than direct genetic selection of transformed cells for resistance to a toxic substance such as an antibiotic. These genes are particularly useful to quantitate or visualize the spatial pattern of expression of the DNA sequence in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase. Jefferson, *Plant Mol. Biol. Rep.* 5:387 (1987); Teeri et al., *EMBO J.* 8:343 (1989); Koncz et al., *Proc. Nat'l Acad. Sci. (USA)* 84:131 (1987); De Block et al, *EMBO J.* 3:1681 (1984). Another approach to the identification of relatively rare transformation events has been use of a gene that encodes a dominant constitutive regulator of the *Zea mays* anthocyanin pigmentation pathway (Ludwig et al., *Science* 247:449 (1990)).

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. The sequence may be inserted in a forward or reverse orientation. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al., *MOLECULAR CLONING, A LABORATORY MANUAL*, 2nd Ed.; Cold Spring Harbor Laboratory Press, Cold Spring Harbor, N.Y. (1989).

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

The vector containing the appropriate DNA sequence as described elsewhere herein, as well as an appropriate promoter and other appropriate control sequences, may be introduced into an appropriate host using a variety of well known techniques suitable to expression therein of a desired polypeptide. The present invention also relates to host cells containing the above-described constructs discussed. The host cell can be a higher eukaryotic cell, such as a mammalian or plant cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, microinjection, cationic lipid-mediated transfection, electroporation, transduction, scrape loading, ballistic introduction, infection or other methods. Such methods are described in many standard laboratory manuals, such as Davis et al., *BASIC METHODS IN MOLECULAR BIOLOGY*, (1986) and Sambrook et al., *MOLECULAR CLONING: A LABORATORY MANUAL*, 2nd Ed., Cold Spring Harbor Laboratory Press, Cold Spring Harbor, N.Y. (1989).

Representative examples of appropriate hosts include bacterial cells, such as streptococci, staphylococci, *E. coli*, streptomyces and *Salmonella typhimurium* cells; fungal cells, such as yeast cells and Aspergillus cells; insect cells such as Drosophila S2 and Spodoptera Sf9 cells; animal cells such as CHO, COS and Bowes melanoma cells; and plant cells. Hosts for a great variety of expression constructs are well known, and those of skill will be enabled by the present disclosure readily to select a host for expressing a polypeptide in accordance with this aspect of the present invention.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well know to those skilled in the art.

As noted above, the present invention provides vectors capable of expressing phytate biosynthetic enzymes under the control of suitable promoters. In general, the vectors should be functional in plant cells. At times, it may be referable to have vectors that are functional in *E. coli* (e.g., production of protein or raising antibodies, DNA sequence analysis, construction of inserts, obtaining quantities of nucleic acids and proteins). Vectors and procedures for cloning and expression in *E. coli* are discussed above and, for example, in Sambrook et al. (supra) and in Ausubel et al. (supra).

Vectors that are functional in plants are preferably binary plasmids derived from Agrobacterium plasmids. Such vectors are capable of transforming plant cells. These vectors contain left and right border sequences that are required for integration into the host (plant) chromosome. At minimum, between these border sequences is the gene to be expressed under control of a promoter. In preferred embodiments, a selectable marker and a reporter gene are also included. For ease of obtaining sufficient quantities of vector, a bacterial origin that allows replication in E. coli is preferred.

In certain preferred embodiments, the vector contains a reporter gene and the structural genes of this invention. The reporter gene should allow ready determination of transformation and expression. The GUS (β-glucuronidase) gene is preferred (U.S. Pat. No. 5,268,463). Other reporter genes, such as β-galactosidase, luciferase, GFP, and the like, are also suitable in the context of this invention. Methods and substrates for assaying expression of each of these genes are well known in the art. The reporter gene should be under control of a promoter that is functional in plants. Such promoters include CaMV 35S promoter, mannopine synthase promoter, ubiquitin promoter and DNA J promoter.

Preferably, the vector contains a selectable marker for identifying transformants. The selectable marker may confer a growth advantage under appropriate conditions. Generally, selectable markers are drug resistance genes, such as neomycin phosphotransferase. Other drug resistance genes are known to those in the art and may be readily substituted. The selectable marker has a linked constitutive or inducible promoter and a termination sequence, including a polyadenylation signal sequence.

Additionally, a bacterial origin of replication and a selectable marker for bacteria are preferably included in the vector. Of the various origins (e.g., colEl, fd phage), a colEl origin of replication is preferred. Most preferred is the origin from the pUC plasmids, which allow high copy number.

A general vector suitable for use in the present invention is based on pBI121 (U.S. Pat. No. 5,432,081) a derivative of pBIN19. Other vectors have been described (U.S. Pat. No. 4,536,475) or may be constructed based on the guidelines presented herein. The plasmid pBI121 contains a left and right border sequence for integration into a plant host chromosome. These border sequences flank two genes. One is a kanamycin resistance gene (neomycin phosphotransferase) driven by a nopaline synthase promoter and using a nopaline synthase polyadenylation site. The second is the E. coli GUS gene under control of the CaMV 35S promoter and polyadenylated using a nopaline synthase polyadenylation site. Plasmid pBI121 also contains a bacterial origin of replication and selectable marker.

In certain embodiments, the vector may contain the structural genes identified herein under control of a promoter. The promoter may be the native promoters associated with the structural genes themselves or a strong, constitutive promoter, such as CaMV 35S promoter. Other elements that are preferred for optimal expression (e.g., transcription termination site, enhancer, splice site) may also be included. The genes may alternatively be expressed as fusion proteins with a reporter gene, for example.

Plant Transformation Methods

As discussed above the present invention also provides methods for producing a plant which expresses a foreign gene, comprising the steps of (a) introducing a vector as described above into an embryogenic plant cell, wherein the vector contains a foreign gene in an expressible form, and (b) producing a plant from the embryogenic plant cell, wherein the plant expresses the foreign gene.

Vectors may be introduced into plant cells by any of several methods. For example, DNA may be introduced as a plasmid by Agrobacterium in co-cultivation or bombardment. Other transformation methods include electroporation, $CaPO_4$-mediated transfection, and the like. Preferably, DNA is first transfected into Agrobacterium and subsequently introduced into plant cells. Most preferably, the infection is achieved by co-cultivation. In part, the choice of transformation methods depends upon the plant to be transformed.

Phytate biosynthetic polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

It is appreciated that the gene expressing the polypeptide of interest may have to be "codon-optimized" to affect efficient expression of a particular host. Thus, this invention contemplates selecting from the sequences below, the particular codon optimized sequence for the particular host cell of interest.

Other genes of interest may be "stacked" during the same transformation events. For example, other genes of interest may impart disease, pest or herbicide resistance, or improve the feed and food quality of the plant or seed, such increased or altered oil expression or altered protein or carbohydrate expression.

Regeneration of Transformed Plants

Following transformation, regeneration is involved to obtain a whole plant from transformed cells. Techniques for regenerating plants from tissue culture such as transformed protoplasts or callus cell lines, are known in the art. For example, see Phillips, et al.; *Plant Cell Tissue Organ Culture;* Vol.1: p 123; (1981); Patterson, et al.; *Plant Sci.;* Vol. 42; p.125; (1985); Wright, et a/.; *Plant Cell Reports;* Vol. 6: p. 83; (1987); and Barwale, et al.; *Planta;* Vol. 167; p. 473 (1986); each incorporated herein in its entirety by reference. The selection of an appropriate method is within the skill of the art.

It is expected that the transformed plants will be used in traditional breeding programs, including TOPCROSS pollination systems as disclosed in U.S. Pat. Nos. 5,706,603 and 5,704,160 the disclosure of each is incorporated herein by reference.

Polynucleotide Assays

This invention is also related to the use of the phytate biosynthetic enzyme polynucleotides in marker to assist in breeding program, as described for example in PCT publication US89/00709. The DNA may be used directly for detection or may be amplified enzymatically by using PCR prior to analysis. PCR (Saiki et al., *Nature* 324:163–166 (1986)). RNA or cDNA may also be used in the same ways. As an example, PCR primers complementary to the nucleic acid encoding the phytate biosynthetic enzymes can be used to identify and analyze phytate biosynthetic enzyme presence and expression. Using PCR, characterization of the gene present in a particular tissue or plant variety may be made by an analysis of the genotype of the tissue or variety. For example, deletions and insertions can be detected by a change in size of the amplified product: in comparison to the genotype of a reference sequence. Point mutations can be identified by hybridizing amplified DNA to radiolabeled phytate biosynthetic enzyme RNA or alternatively, radiolabeled phytate biosynthetic enzyme antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic typing of various varieties of plants based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science,* 230:1242 (1985)).

Sequence changes at specific locations also may be revealed by nuclease protection assays, such as RNase and Si protection or the chemical cleavage method (e.g., Cotton et al., *Proc. Nat'l. Acad. Sci., (USA)*, 85A397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

A mutation may be ascertained for example by a DNA sequencing assay. Samples are processed by methods known in the art to capture the RNA. First strand cDNA is synthesized from the RNA samples by adding an oligonucleotide primer consisting of sequences which hybridize to a region on the mRNA. Reverse transcriptase and deoxynucleotides are added to allow synthesis of the first strand cDNA. Primer sequences are synthesized based on the DNA sequences of the phytate biosynthetic enzymes of the invention. The primer sequence is generally comprised of at least 15 consecutive bases, and may contain at least 30 or even 50 consecutive bases.

Cells carrying mutations or polymorphisms in the gene of the present invention may also be detected at the DNA level by a variety of techniques. The DNA may be used directly for detection or may be amplified enzymatically by using PCR (Saiki et al., *Nature,* 324:163–166 (1986)) prior to analysis. RT-PCR can also be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding phytate biosynthetic enzymes can be used to identify and analyze mutations. Examples of representative primers are shown below in Table 1. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. While perfectly matched sequences can be distinguished from mismatched duplexes by RNase A digestion or by differences in melting temperatures, preferably point mutations are identified by sequence analysis.

Primers used for detection of mutations or polymorphisms in myo-inositol 1-phosphate synthase gene

5'CTCGCTACCTCGCTTCGCATTCCATT3'
5'ACGCCACTTGGCTCACTTGTACTCCA3'

Primers used for detection of mutations or polymorphisms in myo-inositol monophosphatase-3 gene

5'ACGAGGTTGCGGGCGAACCGAAAAT3'
5'TAGGGACCGTTGCCTCAACCTAT3'

Primers used for detection of mutations or polymorphisms in myo-inositol 1,3,4-trisphosphate 5/6-kinase gene

5'TTCTCTCGGTCGCCGCTACTGG3'
5'AGCATGAACAGTTAGCACCT3'

Primers used for detection of mutations or polymorphisms in phosphatidylinositol 3-kinase gene

5'CCGCTTCTCC TCACCTTCCT CT 3'
5'TGGCTTGTGA CAGTCAGCAT GT 3'

The above primers may be used for amplifying phytate biosynthetic enzyme cDNA or genomic clones isolated from a sample derived from an individual plant. The invention also provides the primers above with 1, 2, 3 or 4 nucleotides removed from the 5' and/or the 3' end. The primers may be used to amplify the gene isolated from the individual such that the gene may then be subject to various techniques for elucidation of the DNA sequence. In this way, mutations in the DNA sequence may be identified.

Polypeptide Assays

The present invention also relates to diagnostic assays such as quantitative and diagnostic assays for detecting levels of phytate biosynthetic enzymes in cells and tissues, including determination of normal and abnormal levels. Thus, for instance, a diagnostic assay in accordance with the invention for detecting expression of phytate biosynthetic enzymes compared to normal control tissue samples may be used to detect unacceptable levels of expression. Assay techniques that can be used to determine levels of polypeptides of the present invention, in a sample derived from a plant source are well-known to those of skill in the art. Such assay methods include radioimmunoassay, competitive-binding assays, Western Blot analysis and ELISA assays. Among these ELISAs frequently are preferred. An ELISA assay initially comprises preparing an antibody specific to the polypeptide, preferably a monoclonal antibody. In addition a reporter antibody generally is prepared which binds to the monoclonal antibody. The reporter antibody is attached to a detectable reagent such as radioactive, fluorescent or enzymatic reagent, in this example horseradish peroxidase enzyme.

To carry out an ELISA a sample is removed from a host and incubated on a solid support, e.g., a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any phytate biosynthetic enzymes attached to the polystyrene dish. Unbound monoclonal antibody is washed out with buffer. The reporter antibody linked to horseradish peroxidase is placed in the dish resulting in binding of the reporter antibody to any monoclonal antibody bound to phytate biosynthetic enzyme. Unattached reporter antibody is then washed out. Reagents for peroxidase activity, including a colorimetric substrate are then added to the dish. Immobilized peroxidase, linked to phytate biosynthetic enzyme through the primary and secondary antibodies, produces a colored reaction product. The amount of color developed in a given time period indicates the amount of phytate biosynthetic enzyme present in the sample. Quantitative results typically are obtained by reference to a standard curve.

A competition assay may be employed wherein antibodies specific to phytate biosynthetic enzymes attached to a solid support and labeled enzyme derived from the host are passed over the solid support and the amount of label detected attached to the solid support can be correlated to a quantity of phytate biosynthetic enzyme in the sample.

Antibodies

The polypeptides, their fragments or other derivatives, or analogs thereof, or cells expressing them can be used as immunogens to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., *Nature* 256:495–497 (1975)), the trioma technique, the human B-cell hybridoma technique (Kozbor et al., *Immunology Today* 4:72 (1983)) and the EBV-hybridoma technique to produce human monoclonal antibodies (Cole et al., pg. 77–96 in *MONOCLONAL ANTIBODIES AND CANCER THERAPY,* Alan R. Liss, Inc. (1985)).

Hybridoma cell lines secreting the monoclonal antibody are another aspect of this invention.

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Polypeptide derivatives include antigenically or immunologically equivalent derivatives which form a particular aspect of this invention.

The term 'antigenically equivalent derivative' as used herein encompasses a polypeptide or its equivalent which will be specifically recognized by certain antibodies which, when raised to the protein or polypeptide according to the present invention, interfere with the immediate physical interaction between the antibody and its cognate antigen.

The term "immunologically equivalent derivative" as used herein encompasses a peptide or its equivalent which when used in a suitable formulation to raise antibodies in a vertebrate, the antibodies act to interfere with the immediate physical interaction between the antibody and its cognate antigen The polypeptide, such as an antigenically or immunologically equivalent derivative or a fusion protein thereof is used as an antigen to immunize a mouse or other animal such as a rat guinea pig, goat, rabbit, sheep, cattle or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Alternatively phage display technology could be utilized to select antibody genes with binding activities towards the polypeptide either from repertoires of PCR amplified v-genes of lymphocytes from humans screened for possessing anti-Fbp or from naive libraries (McCafferty, J. et al., (1990), *Nature* 348:552–554; Marks, J. et al., (1992) *Biotechnology* 10:779–783). The affinity of these antibodies can also be improved by chain shuffling (Clackson, T. et al., (1991) *Nature* 352:624–628).

The antibody should be screened again for high affinity to the polypeptide and/or fusion protein.

As mentioned above, a fragment of the final antibody may be prepared.

The antibody may be either intact antibody of $M_r$ approximately 150,000 or a derivative of it, for example a Fab fragment or a Fv fragment as described in Sierra, A and Pluckthun, A., *Science* 240:1038–1040 (1988). If two antigen binding domains are present each domain may be directed against a different epitope—termed 'bispecific' antibodies.

The antibody of the invention, as mentioned above, may be prepared by conventional means for example by established monoclonal antibody technology (Kohler, G. and Milstein, C., *Nature,* 256:495–497 (1975)) or using recombinant means e.g. combinatorial libraries, for example as described in Huse, W. D. et al., *Science* 246:1275–1281 (1989).

Preferably the antibody is prepared by expression of a DNA polymer encoding said antibody in an appropriate expression system such as described above for the expression of polypeptides of the invention. The choice of vector for the expression system will be determined in part by the host, which may be a prokaryotic cell, such as *E. coli* (preferably strain B) or Streptomyces sp. or a eukaryotic cell, such as a mouse C127, mouse myeloma, human HeLa, Chinese hamster ovary, filamentous or unicellular fungi or insect cell. The host may also be a transgenic animal or a transgenic plant for example as described in Hiatt, A. et al., *Nature* 340:76–78 (1989). Suitable vectors include plasmids, bacteriophages, cosmids and recombinant viruses, derived from, for example, baculoviruses and vaccinia.

The Fab fragment may also be prepared from its parent monoclonal antibody by enzyme treatment, for example using papain to cleave the Fab portion from the Fc portion.
Phytate Biosynthetic Enzyme Binding Molecules and Assays This invention also provides a method for identification of molecules, such as binding molecules, that bind the phytate biosynthetic enzymes. Genes encoding proteins that bind the enzymes, such as binding proteins, can be identified by numerous methods known to those of skill in the art, for example, ligand panning and FACS sorting. Such methods are described in many laboratory manuals such as, for instance, Coligan et al., *Current Protocols in Immunology* 1(2): Chapter 5 (1991).

For instance, expression cloning may be employed for this purpose. To this end polyadenylated RNA is prepared from a cell expressing the phytate biosynthetic enzymes, a cDNA library is created from this RNA, the library is divided into pools and the pools are transfected individually into cells that are not expressing the enzyme. The transfected cells then are exposed to labeled enzyme. The enzyme can be labeled by a variety of well-known techniques including standard methods of radio-iodination or inclusion of a recognition site for a site-specific protein kinase. Following exposure, the cells are fixed and binding of enzyme is determined. These procedures conveniently are carried out on glass slides.

Pools are identified of cDNA that produced phytate biosynthetic enzyme-binding cells. Sub-pools are prepared from these positives, transfected into host cells and screened as described above. Using an iterative sub-pooling and re-screening process, one or more single clones that encode the putative binding molecule can be isolated.

Alternatively a labeled ligand can be photo affinity linked to a cell extract, such as a membrane or a membrane extract, prepared from cells that express a molecule that it binds, such as a binding molecule. Cross-linked material is resolved by polyacrylamide gel electrophoresis ("PAGE") and exposed to X-ray film. The labeled complex containing the ligand-binding can be excised, resolved into peptide fragments, and subjected to protein microsequencing. The amino acid sequence obtained from microsequencing can be used to design unique or degenerate oligonucleotide probes to screen cDNA libraries to identify genes encoding the putative binding molecule.

Polypeptides of the invention also can be used to assess phytate biosynthetic enzyme binding capacity of phytate biosynthetic enzyme binding molecules, such as binding molecules, in cells or in cell-free preparations.

Polypeptides of the invention may also be used to assess the binding or small molecule substrates and ligands in, for example, cells, cell-free preparations, chemical libraries, and natural product mixtures. These substrates and ligands may be natural substrates and ligands or may be structural or functional mimetics.

Anti-phytate biosynthetic enzyme antibodies represent a useful class of binding molecules contemplated by this invention.
Antagonists—Assays and Molecules The invention also provides a method of screening compounds to identify those which enhance or block the action of phytate biosynthetic enzymes on cells, such as its interaction with substrate molecules. An antagonist is a compound which decreases the natural biological functions of the enzymes.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing phytate biosynthetic enzyme-induced activities, thereby preventing the action of the enzyme by excluding the enzyme from binding.

Potential antagonists include a small molecule which binds to and occupies the binding site of the polypeptide thereby preventing binding to cellular binding molecules, such as binding molecules, such that normal biological activity is prevented. Examples of small molecules include but are not limited to small organic molecules, peptides or peptide-like molecules.

Other potential antagonists include molecules that affect the expression of the gene encoding phytate biosynthetic enzymes (e.g. transactivation inhibitors). Other potential antagonists include antisense molecules. Antisense technology can be used to control gene expression through antisense DNA or RNA or through double- or triple-helix formation. Antisense techniques are discussed, for example, in—Okano, J. Neurochem. 56: 560 (1991); *OLIGODEOXY-NUCLEOTIDES AS ANTISENSE INHIBITORS OF GENE EXPRESSION,* CRC Press, Boca Raton, Fla. (1988). Triple helix formation is discussed in, for instance Lee et al, *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of phytate biosynthetic enzymes. The antisense RNA oligonucleotide hybridizes to the mRNA in vivo and blocks translation of the mRNA molecule into phytate biosynthetic enzymes. The oligonucleotides described above can also be delivered to cells such that the antisense RNA or DNA may be expressed in vivo to inhibit production of phytate biosynthetic enzymes.

The antagonists may be employed for instance to reduce the levels of phytate and/or increase the available phosphorous in plant cells.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., *MOLECULAR CLONING:A LABORA-*

TORY MANUAL, 2nd Ed.; Cold Spring Harbor Laboratory Press, Cold Spring Harbor, N.Y. (1989).

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook et al., *MOLECULAR CLONING: A LABORATORY MANUAL*, 2nd Ed., Cold Spring Harbor Laboratory Press, Cold Spring Harbor, N.Y. (1989) and numerous other references such as, for instance, by Goeddel et al, *Nucleic Acids Res.* 8:4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 microgram of DNA.

Example 1

Isolation of DNA Coding for Novel Proteins from *Zea mays*

The polynucleotide having the myo-inositol 1-phosphate synthase DNA sequence was obtained from the sequencing of a library of cDNA clones prepared from maize embryos isolated 15 days after pollination. The polynucleotide having the myo-inositol monophosphatase-3 DNA sequence was obtained from the sequencing of a library of cDNA clones prepared from maize immature ears. The polynucleotide having the myo-inositol 1,3,4-triphosphate 5.6-kinase DNA sequence was obtained from the sequencing of a library of cDNA clones prepared from maize tassel shoots. The polynucleotide having the phosphatidylinositol-3-kinase DNA sequence was obtained from the sequencing of a library of cDNA clones prepared from germinating maize seeds. Total RNA was isolated from this tissue using standard protocols and enriched for mRNA by selection with oligo dT, again by standard protocols. This mRNA was then used as template to synthesize complementary DNA (cDNA) using the enzyme reverse transcriptase by conventional methods. The resulting strand of cDNA was then converted to double-stranded pieces of cDNA and ligated into the cloning vector pSPORT using conventional ligation/transformation methods. Individual colonies were then selected and plasmid DNA prepared from each. This plasmid DNA was then denatured and used as template in dideoxynucleotide sequencing reactions. By sequencing the individual clones thus identified with sequencing primers designed from the original sequence it is then possible to extend the sequence in both directions to determine the full gene sequence. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (See Screening By Hybridization 1.90 and Sequencing Denatured Double-Stranded DNA Templates 13.70). The sequences were compared to those sequences available in public databases (i.e., Genbank) to determine homologies/gene identification. In some cases the sequencing data from two or more clones containing overlapping segments of DNA were used to construct the contiguous DNA sequence below.

Example 2

Construction of Expression Cassettes for Homology-Dependent Gene Silencing of Phytate Biosynthetic Enzyme Expression To facilitate manipulations of this trait in conventional breeding programs, the expression cassette described above is used in homologous gene silencing (i.e. Knockout) of the endogenous phytate biosynthetic enzyme polynucleotides by using the embryo-preferred promoter globulin-1 to drive expression of the genes.

Plant expression cassettes are made using the embryo-preferred promoter globulin-1 to drive expression of the phytate biosynthetic enzyme polynucleotides. Globulin-1 termination sequences are also included in this cassette. The entire expression cassette is cloned into a pUC based plasmid vector for easy manipulation in *E. coli*. This construct is used for particle bombardment transformation of corn in conjunction with another expression construct which includes a selectable marker (for example Pat, PHP8092→Ubi::mo-PAT::ubi). For Agrobacterium-mediated transformation, a plasmid is moved into an appropriate binary vector containing both left and right border sequences to facilitate DNA transfer into the target genome.

This polynucleotide, encoding the inventive polypeptides, when made to be non-functional in plants, results in a reduction in phytic acid and an increase in non-phytate phosphorus levels. This can be demonstrated using the transposable element Mu. Maize lines are confirmed as having a Mu element inserted into the coding region of the phytate biosynthetic enzyme polynucleotides. Extensive genetics are done on this phenotype demonstrating it to be transmitted to progeny as a homozygous recessive trait.

Example 3

Transformation of Maize

The inventive polynucleotides contained within a vector are transformed into embryogenic maize callus by particle bombardment. Transgenic maize plants are produced by bombardment of embryogenically responsive immature embryos with tungsten particles associated with DNA plasmids. The plasmids consist of a selectable and an unselectable marker gene.

Preparation of Particles

Fifteen mg of tungsten particles (General Electric), 0.5 to 1.8μ, preferably 1 to 1.8μ, and most preferably 1μ, are added to 2 ml of concentrated nitric acid. This suspension was sonicated at 0° C. for 20 minutes (Branson Sonifier Model 450, 40% output, constant duty cycle). Tungsten particles are pelleted by centrifugation at 10000 rpm (Biofuge) for one minute, and the supernatant is removed. Two milliliters of sterile distilled water are added to the pellet, and brief sonication is used to resuspend the particles. The suspension is pelleted, one milliliter of absolute ethanol is added to the pellet, and brief sonication is used to resuspend the particles. Rinsing, pelleting, and resuspending of the particles is performed two more times with sterile distilled water, and finally the particles are resuspended in two milliliters of sterile distilled water. The particles are subdivided into 250-ml aliquots and stored frozen.

Preparation of Particle-Plasmid DNA Association

The stock of tungsten particles are sonicated briefly in a water bath sonicator (Branson Sonifier Model 450, 20% output, constant duty cycle) and 50 ml is transferred to a microfuge tube. Equimolar amounts of selectable and unselectable plasmid DNA are added to the particles for a final DNA amount of 0.1 to 10 mg in 10 ml total volume, and briefly sonicated. Preferably, 1 mg total DNA is used. Specifically, 4.9 ml of PHP 8092 (Ubiquitin::ubiquitin intron::mo-PAT::35S CaMV, 6.329 kbp)) plus 5.1 ml of (globulin1::mi1ps::globulin1), where any phytate biosynthetic enzyme polynucleotide can replace mi1ps, both at 0.1 mg/ml in TE buffer, are added to the particle suspension.

Fifty microliters of sterile aqueous 2.5 M $CaCl_2$ are added, and the mixture is briefly sonicated and vortexed. Twenty microliters of sterile aqueous 0.1 M spermidine are added and the mixture is briefly sonicated and vortexed. The mixture is incubated at room temperature for 20 minutes with intermittent brief sonication. The particle suspension is centrifuged, and the supernatant is removed. Two hundred fifty microliters of absolute ethanol are added to the pellet, followed by brief sonication. The suspension is pelleted, the supernatant is removed, and 60 ml of absolute ethanol are added. The suspension is sonicated briefly before loading the particle-DNA agglomeration onto macrocarriers.

Preparation of Tissue

Immature embryos of maize variety High Type II are the target for particle bombardment-mediated transformation. This genotype is the $F_1$ of two purebred genetic lines, parents A and B, derived from the cross of two know maize inbreds, A188 and B73. Both parents are selected for high competence of somatic embryogenesis, according to Armstrong et al, *Maize Genetics Coop. News* 65:92 (1991).

Ears from $F_1$ plants are selfed or sibbed, and embryos are aseptically dissected from developing caryopses when the scutellum first became opaque. This stage occurs about 9–13 days post-pollination, and most generally about 10 days post-pollination, depending on growth conditions. The embryos are about 0.75 to 1.5 millimeters long. Ears are surface sterilized with 20–50% Clorox for 30 minutes, followed by three rinses with sterile distilled water.

Immature embryos are cultured with the scutellum oriented upward, on embryogenic induction medium comprised of N6 basal salts, Eriksson vitamins, 0.5 mg/l thiamine HCl, 30 gm/l sucrose, :2.88 gm/l L-proline, 1 mg/l 2,4-dichlorophenoxyaceticacid, 2 gm/l Gelrite, and 8.5 mg/l $AgNO_3$. Chu et al, *Sci. Sin.* 18:659 (1975); Eriksson, *Physiol. Plant* 18:976 (1965). The medium is sterilized by autoclaving at 121° C. for 15 minutes and dispensed into 100×25 mm Petri dishes. $AgNO_3$ is filter-sterilized and added to the medium after autoclaving. The tissues are cultured in complete darkness at 28° C. After about 3 to 7 days, most usually about 4 days, the scutellum of the embryo swells to about double its original size and the protuberances at the coleorhizal surface of the scutellum indicated the inception of embryogenic tissue. Up to 100% of the embryos displayed this response, but most commonly, the embryogenic response frequency is about 80%.

When the embryogenic response is observed, the embryos are transferred to a medium comprised of induction medium modified to contain 120 gm/l sucrose. The embryos are oriented with the coleorhizal pole, the embryogenically responsive tissue, upwards from the culture medium. Ten embryos per Petri dish are located in the center of a Petri dish in an area about 2 cm in diameter. The embryos are maintained on this medium for 3–16 hour, preferably 4 hours, in complete darkness at 28° C. just prior to bombardment with particles associated with plasmid DNAs containing the selectable and unselectable marker genes.

To effect particle bombardment of embryos, the particle-DNA agglomerates are accelerated using a DuPont PDS-1000 particle acceleration device. The particle-DNA agglomeration is briefly sonicated and 10 ml were deposited on macrocarriers and the ethanol is allowed to evaporate. The macrocarrier is accelerated onto a stainless-steel stopping screen by the rupture of a polymer diaphragm (rupture disk). Rupture is effected by pressurized helium. The velocity of particle-DNA acceleration is determined based on the rupture disk breaking pressure. Rupture disk pressures of 200 to 1800 psi are used, with 650 to 1100 psi being preferred, and about 900 psi being most highly preferred. Multiple disks are used to effect a range of rupture pressures.

The shelf containing the plate with embryos is placed 5.1 cm below the bottom of the macrocarrier platform (shelf #3). To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A Petri dish with the target embryos is placed into the vacuum-i chamber and located in the projected path of accelerated particles. A vacuum is created in the chamber, preferably about 28 in Hg. After operation of the device, the vacuum is released and the Petri dish is removed.

Bombarded embryos remain on the osmotically-adjusted medium during bombardment, and 1 to 4 days subsequently. The embryos are transferred to selection medium comprised of N6 basal salts, Eriksson vitamins, 0.5 mg/1 thiamine HCl, 30 gm/l sucrose, 1 mg/l 2,4-dichlorophenoxyacetic acid, 2 gm/l Gelrite, 0.85 mg/l Ag $NO_3$ and 3 mg/l bialaphos (Herbiace, Meiji). Bialaphos is added filter-sterilized. The embryos are subcultured to fresh selection medium at 10 to 14 day intervals. After about 7 weeks, embryogenic tissue, putatively transformed for both selectable and unselected marker genes, proliferates from about 7% of the bombarded embryos. Putative transgenic tissue is rescued, and that tissue derived from individual embryos is considered to be an event and is propagated independently on selection medium. Two cycles of clonal propagation are achieved by visual selection for the smallest contiguous fragments of organized embryogenic tissue.

A sample of tissue from each event is processed to recover DNA. The DNA is restricted with a restriction endonuclease and probed with primer sequences designed to amplify DNA sequences overlapping the phytate biosynthetic enzymes and non-phytate biosynthetic enzyme portion of the plasmid. Embryogenic tissue with amplifiable sequence is advanced to plant regeneration.

For regeneration of transgenic plants, embryogenic tissue is subcultured to a medium comprising MS salts and vitamins (Murashige & Skoog, *Physiol. Plant* 15: 473 (1962)), 100 mg/l myo-inositol, 60 gm/l sucrose, 3 gm/l Gelrite, 0.5 mg/l zeatin, 1 mg/l indole-3-acetic acid, 26.4 ng/l cis-trans-abscissic acid, and 3 mg/l bialaphos in 100×25 mm Petri dishes, and is incubated in darkness at 28° C. until the development of well-formed, matured somatic embryos can be seen. This requires about 14 days. Well-formed somatic embryos are opaque and cream-colored, and are comprised of an identifiable scutellum and coleoptile. The embryos are individually subcultured to a germination medium comprising MS salts and vitamins, 100 mg/l myo-inositol, 40 gm/l sucrose and 1.5 gm/l Gelrite in 100×25 mm Petri dishes and incubated under a 16 hour light:8 hour dark photoperiod and 40 meinsteinsm$^{-2}$sec$^{-1}$ from cool-white fluorescent tubes. After about 7 days, the somatic embryos have germinated and produced a well-defined shoot and root. The individual plants are subcultured to germination medium in 125×25 mm glass tubes to allow further plant development. The plants are maintained under a 16 hour light:8 hour dark photoperiod and 40 meinsteinsm$^{-2}$sec$^{-1}$ from cool-white fluorescent tubes. After about 7 days, the plants are well-established and are transplanted to horticultural soil, hardened off, and potted into commercial greenhouse soil mixture and grown to sexual maturity in a greenhouse. An elite inbred line is used as a male to pollinate regenerated transgenic plants.

Example 4

Identification of High Phosphorus Transgenic Corn Lines

The resulting transformants are screened for elevated levels of inorganic phosphorus using a simple colorimetric assay. Individual transgenic kernels are crushed in the well of a megatiter breeding tray using a hydraulic press to 2000 psi. The crushed kernels are then soaked in 2 ml of 1 N H2SO4 for 2 hours at room temperature. Color development is then initiated by the addition of 4 ml of developing solution (1 part 10% ascorbic acid, 6 parts 0.42% ammonium molybdate in 1N H2SO4) to each crushed kernel. Kernels are scored after 30 minute incubation at room temperature as either positive (blue) or negative (clear). Positive in this instance refers to a high level of inorganic phosphorus. This protocol is a modified version of what is described in Chen et al., *Anal. Chem.* 28:1756 (1956). Those transformants which are screened as positive with the calorimetric assay will then be subjected to more rigorous analyses to include Southern, Northern and Western blotting and quantitation of phytic acid levels.

Confirmation of Elevated Non-Phytate Phosphorus Levels

The present transgenics preferably have non-phytate phosphorus levels in excessive of the natural levels of available phosphorus for the plant species of interest. In respect to corn it is preferred to have non-phytate phosphorus levels of about 0.175%, more preferably about 0.2% and most preferably about 0.225% or higher. These percentages being base on % wt/wt at a 13% moisture basis for both corn seed. With respect to soybeans, it is preferred to have non-phytate phosphorus levels of about 0.47%, more preferably about 0.49% and most preferably about 0.51%. These latter percentage being based on the weight of non-phytate phosphorus/(non phytate P/gram of meal on a 13% moisture basis).

Each plant identified as a potential high phosphorus transgenic is tested again to confirm the original elevated phosphorus reading. Some putative transgenics may not confirm for the elevated phosphorus trait. Those which confirm are selected on the basis of uniformity for the elevated phosphorus trait.

Confirmation of Reduced Phytate Levels

To determine whether high non-phytate phosphorus transgenics are also characterizes by reduced levels of phytate, the following method is used to quantify the level of phytic acid in a tested sample.

The sample is ground, placed in a conical plastic centrifuge tube and treated with hydrochloric acid. It is homogenized with polytron, and extracted at room temperature with vortexing. The extracted sample is placed in a clinical centrifuge at 2500 RPM for 15 minutes. 2.5 ml of the supernatant is removed and added to 25 ml water. The sample is washed through a SAX® column. The column is washed with HCl, eluted and evaporated to dryness. The dried sample is resuspended in water and filtered through a 0.45 micrometer syringe tip filter into a vial. 10 to 20 microliters of samples are prepared to inject into an HPLC column.

The eluting solvent is prepared by mixing 515 ml of methanol, 485 ml of double distilled water, 8 ml tetrabutyl ammonium hydroxide 40% (TBAH), 200 microliters of 10 N, (5 M) sulfuric acid, 0.5 ml formic acid and 1–3 mg phytic acid. Phytic acid is prepared by placing 16 mg of sodium phytate in 5 ml of water. This solution is placed on Dowex ion exchange resin (1 ml Dowex-50 acid form on glass wool in 5 ml pipette tip). This is rinsed with 1–2 ml water, and the filtrate brought to 10 ml with water. Concentration is 1 mg/ml phytic acid. 2 ml is used for 1 liter of solvent. pH of the solvent is adjusted to 4.10 +/–0.05 with 10 N sulfuric acid. Chromatography is accomplished by pumping the sample through a Hamilton PRP-1 reverse phase HPLC column heated to 40 degrees centigrade at a rate of 1 ml per minute. The detection of inositol phosphate is accomplished with a refractive index detector (Waters), which is auto-zeroed at least two (2) minutes before each run.

The confirmed high phosphorus transgenics are tested in this manner.

Some, but not all, of the mutants evaluated in this way are confirmed to be low in phytate.

Sequence Description

SEQ ID NO:1 PHOSPHATIDYLINOSITOL-3-KINASE cDNA
SEQ ID NO:2 PHOSPHATIDYLINOSITOL-3-KINASE POLYPEPTIDE
SEQ ID NO:3 PHOSPHATIDYLINOSITOL-3-KINASE PRIMER
SEQ ID NO:4 PHOSPHATIDYLINOSITOL-3-KINASE PRIMER
SEQ ID NO:5 MYO-INOSITOL 1,3,4-TRIPHOSPHATE 5/6-KINASE cDNA
SEQ ID NO:6 MYO-INOSITOL 1,3,4-TRIPHOSPHATE 5/6-KINASE POLYPEPTIDE
SEQ ID NO:7 MYO-INOSITOL 1,3,4-TRIPHOSPHATE 5/6-KINASE GENERIC
SEQ ID NO:8 MYO-INOSITOL 1,3,4-TRIPHOSPHATE 5/6-KINASE PRIMER
SEQ ID NO:9 MYO-INOSITOL 1,3,4-TRIPHOSPHATE 5/6-KINASE PRIMER
SEQ ID NO:10 MYO-INOSITOL 1-PHOSPHATE SYNTHASE cDNA
SEQ ID NO:11 MYO-INOSITOL 1-PHOSPHATE SYNTHASE POLYPEPTIDE
SEQ ID NO:12 MYO-INOSITOL 1-PHOSPHATE SYNTHASE PRIMER
SEQ ID NO:13 MYO-INOSITOL 1-PHOSPHATE SYNTHASE PRIMER
SEQ ID NO:14 MYO-INOSITOL 1-PHOSPHATE SYNTHASE GENOMIC
SEQ ID NO:15 MYO-INOSITOL 1-PHOSPHATE SYNTHASE GENOMIC
SEQ ID NO:16 MYO-INOSITOL MONOPHOSPHATE-3 cDNA
SEQ ID NO:17 MYO-INOSITOL MONOPHOSPHATE-3 POLYPEPTIDE
SEQ ID NO:18 MYO-INOSITOL MONOPHOSPHATE-3 PRIMER
SEQ ID NO:19 MYO-INOSITOL MONOPHOSPHATE-3 PRIMER
SEQ ID NO:20 INOSITOL POLYPHOSPHATE 5-PHOSPHATASE cDNA
SEQ ID NO:21 D-MYO-INOSITOL-3-PHOSPHATE SYNTHASE cDNA
SEQ ID NO:22 1D-MYO-INOSITOL TRIPHOSPHATE 3-KINASE B cDNA
SEQ ID NO:23 MYO-INOSITOL TRANSPORTER cDNA
SEQ ID NO:24 MAIZE PHYTASE cDNA
SEQ ID NO:25 PHOSPHATIDYLINOSITOL TRANSFER PROTEIN cDNA
SEQ ID NO:26 PHOSPHATIDYLOINOSITOL-4-PHOSPHATE-5-KINASE cDNA
SEQ ID NO:27 PHOSPHATIDYLINOSITOL-SPECIFIC PHOSPHOLIPASE C cDNA
SEQ ID NO:28 MYO-INOSITOL MONOPHOSPHATASE-1 cDNA
SEQ ID NO:29 PHOSPHATIDYLINOSITOL 4-KINASE cDNA
SEQ ID NO:30 PHOSPHATIDYLINOSITOL (4,5) BIS-PHOSPHATE 5-PHOSPHATASE
SEQ ID NO: 31 PHOSPHATIDYLINOSITOL SYNTHASE cDNA

What is claimed is:

1. An isolated polypeptide comprising an amino acid sequence which has at least 90% sequence identity to SEQ ID NO:11, wherein said polypeptide has myo-inositol 1-phosphate synthase activity.

2. The isolated polypeptide of claim 1 which comprises the sequence of SEQ ID NO: 11.

* * * * *